US012569482B2

(12) United States Patent
Liang

(10) Patent No.: US 12,569,482 B2
(45) Date of Patent: Mar. 10, 2026

(54) METHODS AND COMPOSITIONS FOR TREATING IDIOPATHIC PULMONARY FIBROSIS

(71) Applicant: Gui-Bai Liang, Scotch Plains, NJ (US)

(72) Inventor: Gui-Bai Liang, Scotch Plains, NJ (US)

( * ) Notice: Subject to any disclaimer, the term of this patent is extended or adjusted under 35 U.S.C. 154(b) by 234 days.

(21) Appl. No.: 17/062,291

(22) Filed: Oct. 2, 2020

(65) Prior Publication Data

US 2021/0023079 A1     Jan. 28, 2021

Related U.S. Application Data

(63) Continuation of application No. 16/357,293, filed on Mar. 18, 2019, now abandoned.

(60) Provisional application No. 62/644,596, filed on Mar. 19, 2018.

(51) Int. Cl.
| | |
|---|---|
| *A61K 31/496* | (2006.01) |
| *A61K 9/00* | (2006.01) |
| *A61K 31/4418* | (2006.01) |
| *A61P 11/00* | (2006.01) |

(52) U.S. Cl.
CPC .......... *A61K 31/496* (2013.01); *A61K 9/0078* (2013.01); *A61K 31/4418* (2013.01); *A61P 11/00* (2018.01)

(58) Field of Classification Search
CPC .............. A61K 31/4418; A61K 31/496; A61K 9/0078; A61K 2300/00; A61P 11/00; H01L 21/67259; H01L 21/67715; H01L 21/682; H01L 21/6838; H01L 21/68742; H01L 21/6875
See application file for complete search history.

(56) References Cited

U.S. PATENT DOCUMENTS

| | | | |
|---|---|---|---|
| 2011/0190245 A1 | 8/2011 | Schlichthaar | |
| 2012/0244206 A1 | 9/2012 | Cipolla et al. | |
| 2013/0330400 A1 | 12/2013 | Perkins et al. | |
| 2017/0217943 A1 | 8/2017 | Lairson et al. | |
| 2017/0362211 A1 | 12/2017 | Lairson et al. | |

FOREIGN PATENT DOCUMENTS

| | | |
|---|---|---|
| CN | 105392364 A | 3/2016 |
| EP | 1894559 A1 | 5/2008 |
| JP | 2010-507658 A | 3/2010 |
| JP | 2011513258 A | 4/2011 |
| JP | 2015-517576 A | 6/2015 |
| JP | 201656202 A | 4/2016 |
| WO | 2014197738 A1 | 12/2014 |

OTHER PUBLICATIONS

Darquenne, Aerosol Deposition in Health and Disease. Journal of Aerosol Medicine and Pulmonary Drug Delivery, vol. 25(3) pp. 140-147 (Year: 2012).*
Borghardt et al., Inhaled therapy in respiratory disease: The complex interplay of pulmonary kinetic processes. Canadian Respiratory Journal, pp. 1-11 (Year: 2018).*
Ivanova et al., Inhalation treatment of pulmonary fibrosis by liposomal prostaglandin E2. Eur. J. Pharm. Biopharm., vol. 84(2), pp. 335-344 (Year: 2013).*
JPO, Notice of Reasons for Rejection of counterpart JP Application No. 2020-544611 Oct. 12, 2021.
European search report and written opinion of the counterpart EP Application No. 19772469, Oct. 27, 2021.
Jason M. Vaughn et al., Single dose and multiple dose studies of itraconazole nanoparticles, Eur J Pharm Biopharm. Jun. 2006;63(2):95-102.
Chioma et al., Role of Microbial Agents in Pulmonary Fibrosis, Yale J of Biology and Medicine (2017) vol. 90, pp. 219-227.
Bollong et al., PNAS, 114 (May 2, 2017) 4679-4684.
Richeldi et al., N Engl J Med (May 29, 2014) vol. 370, No. 22, p. 2071-2082.
Mash et al., Inhaled versus oral steroids for adults with chronic asthma, Cochrane Database of 11 Systematic Reviews, Jan. 22, 2001 [retrieved on Apr. 30, 2019].
PCT/US2019/022827 International Search Report and Written Opinion of the International Searching Authority dated May 14, 2019.
JPO Examination report after appeal dated Oct. 18, 2022 issued in counterpart JP application 2020-544611.
CNPIA, First Office Action of CN201980020504.0, the counterpart application filed with CNPIA, Nov. 30, 2022.

* cited by examiner

*Primary Examiner* — Jean P Cornet

(74) *Attorney, Agent, or Firm* — Lewis Roca Rothgerber Christie LLP

(57)     ABSTRACT

Provided is a pharmaceutical composition comprising an effective amount of itraconazole, and a pharmaceutically acceptable excipient. The use of the pharmaceutical composition for treatment of idiopathic pulmonary fibrosis is also provided.

10 Claims, 6 Drawing Sheets

METHODS AND COMPOSITIONS FOR TREATING IDIOPATHIC PULMONARY FIBROSIS

CROSS REFERENCE TO RELATED APPLICATIONS

This application is a continuation of U.S. application Ser. No. 16/357,293 filed Mar. 18, 2019 and which claims the benefit of priority to U.S. provisional Application No. 62/644,596 filed Mar. 19, 2018, the disclosure of which is incorporated by reference in its entirety.

BACKGROUND OF THE INVENTION

Idiopathic Pulmonary Fibrosis (IPF) is a chronic and progressive lung disease that results in respiratory failure and death. IPF is the most common cause of death from progressive lung disease, and affects about 5 million people worldwide. An estimated median survival after diagnosis is only 2-3 years (Chakraborty et al., (2014) *Expert Opin Investig Drugs,* 23:893-910; Spagnolo et al., (2015) *Pharmacology & Therapeutics* 152:18-27; Tzouvelekis et al., (2015) *Therapeutics and Clinical Risk Management* 11:359-370). In the United States, as many as 89,000 people are afflicted with IPF, with about 34,000 newly diagnosed annually (Raghu G et al., (2006) *Am J Respir Crit Care Med* 174: (7):810-816). Prevalence of IPF ranges from 14.0 to 42.7 cases per 100,000 persons and the annual incidence ranges from 6.8 to 16.3 cases per 100,000 persons, depending on the strictness of the diagnostic criteria employed (Raghu G et al., supra.). The prevalence of IPF increases with age, with most IPF patients at the age of 60 years or even older at the time of diagnosis. The disease is more common in men than in women (Fernandez Perez E R et al., (2010) *Chest* 137(1):129-137), with most patients being current or former smokers. A familial form of IPF may account for as many as 20% of IPF cases (Loyd J E, (2008) *Eur Respir Rev* 17(109):163-167).

The etiology of IPF remains unknown. Potential factors, such as cigarette smoking, dust exposure and infection agents, however, have been associated with the development of IPF. IPF is characterized by progressive and irreversible distortion of the lung's architecture as a result of apoptosis of epithelial and endothelial cells, fibroblast hyperplasia and extracellular metric remodeling (Chakraborty et al., (2014) *Expert Opin Investig Drugs,* 23:893-910). As interstitial fibrosis advances with accompanying distortion of lung architecture, the lung becomes less compliant, increasing the effort associated with breathing, leading to dyspnea. Typically, lung function declines slowly over time, but some patients experience rapid declines that can lead to hospitalization or death, particularly in later stages of the disease.

Development of agents for treatment of IPF has been slow in progress. The first two agents for treating IPF, pirfenidone and nintedanib, were approved only at the end of 2014 (King et al., (2014)*N Engl J Med* 370:2083-92; Richeldi et al., (2014) *N Engl J Med* 370:2071-82). These two agents, however, have only limited efficacy and significant side effects, and require complicated dosing regimen. Recently conducted phase 3 clinical trials of pirfenidone, sildenafil, bosentan, etanercept, and interferon gamma-1b failed to demonstrate efficacy in their primary endpoints. N-acetyl cysteine (NAC), corticosteroids, and the immunosuppressive drugs cyclophosphamide and azathioprine are commonly prescribed, but there is little evidence that use of these drugs improves patient outcome or alters the natural course of the disease (Collard H R et al., (2004) *Chest* 125(6):2169-2174; Walter N et al., (2006) *Proc Am Thorac Soc* 3(4):377-381). In fact, the combination of prednisone, azathioprine, and NAC produced a worse outcome than NAC or placebo in a recent IPF study (NIH News, Oct. 24, 2011). Lung transplantation is the only treatment that improves survival (Walter N et al, supra.), but most IPF patients are not eligible for transplantation because of their age or comorbid conditions. IPF patients usually are managed with supportive measures such as symptomatic treatment of cough and dyspnea, supplemental oxygen for hypoxemia, smoking cessation, pulmonary rehabilitation, and prophylaxis and control of respiratory tract infections.

The progressive and fatal course of IPF coupled with the absence of approved drugs underscore the need for new methods and agents to treat this devastating disease. The present invention meets this unmet medical need by providing novel methods and agents for use in treating IPF.

Itraconazole is an imidazole/triazole type antifungal agent. Recently, Bollong et al. (2017) described an image-based assay of screening for novel anti-fibrotic compounds, and identified itraconazole to be active (Bollong et al., (2017) *PNAS,* 114 (18): 4679-4684). However, in U.S. Patent Publication No. 20170362211, the same group of researchers pointed out that, even though itraconazole may have efficacy in both bleomycin-induced lung and carbon tetrachloride-induced liver fibrosis mouse models, the drug's use as an anti-fibrotic is limited due to known adverse effects, such as P450 inhibition.

Itraconazole is known to be a highly selective inhibitor of cytochrome P-450 sterol C-14 α-demethylation (Perfect J R, (2017) *Nature Review Drug Discovery* 16:603-616), and to have inhibitory activity toward both the hedgehog signaling pathway (Kim J et al., (2010) *Cancer Cell.* 17:388-399; Horn A et al., (2012) *Arthritis Rheum.* 64:2724-2733; Bolanos A L et al., (2012) *Am J Physiol Lung Cell Mol Physiol.* 303:L978-L990) and angiogenesis (Chong et al., (2007) *ACS Chem Biol.* 2:263-70). Itraconazole was also reported to have inhibitory activities in the vascular endothelial growth factor receptor 2 signaling in endothelial cells (Nacev B A et al., (2011) *J Biol Chem.* 286:44045-44056; Chaudhary N I et al., (2007) *EurRespir J.* 29:976-985). As itraconazole is an FDA approved drug with a well characterized safety and tolerance profile, researchers named as inventors of US20170362211 apparently have found that the doses and/or blood levels of itraconazole needed for fibrosis treatment exceeded the safety profile/doses approved by FDA. These researchers instead directed their further efforts to developing a new class of derivatives of itraconazole for the treatment of multiple fibrosis related diseases.

SUMMARY OF THE INVENTION

The present inventors have surprisingly discovered that with a suitable dosing regimen or a novel administration route, itraconazole can be used to prevent or treat IPF in an effective and safe manner.

Accordingly, in one embodiment, the present invention provides a method for treating idiopathic pulmonary fibrosis, by administering to a patient in need thereof, a pharmaceutical composition comprising an effective amount of itraconazole, and a pharmaceutically acceptable excipient. In one embodiment, the daily dose of itraconazole is in the range of 20 mg to 1200 mg for an adult human patient.

In one embodiment, the method of the invention comprises administering itraconazole in combination with an effective amount of one or more known antifibrosis agents, e.g. pirfenidone and nintedanib.

In one embodiment, the method of the invention comprises administering a daily dose of itraconazole of 0.5 mg/kg to 200 mg/kg bodyweight. Itraconazole may be administered by any suitable means for oral, parenteral, rectal, cutaneous, nasal, vaginal, or inhalant use.

In one embodiment, the pharmaceutical composition is delivered using an inhaler directly into the lungs of the patient, for example, at a level that is less than about $\frac{1}{10}$ of an oral dosage. In another embodiment, the pharmaceutical composition is in a dosage form of a spray, or a nebulizer.

Also provided are pharmaceutical compositions for treating IPF comprising an amount of itraconazole effective for treating IPF, and a pharmaceutically acceptable excipient. In one embodiment, the daily dose of itraconazole is in the range of 20 mg to 1200 mg.

Although inhalable formulations of itraconazole is known, see e.g. U.S. Pat. No. 9,061,027, and review by Le and Schiller (Le and Schiller, (2010) *Curr Fungal Infect Rep.* 4:96-102), they were only formulated for anti-fungal purposes, and had not been formulated for long-term, low dose usages as required for IPF treatment or prophylactics. Using a new nanotechnology technique that spray-freezes a drug with poor water solubility into a liquid, the effectiveness of aerosolized itraconazole as a prophylactic agent against invasive pulmonary aspergillosis caused by *Aspergillus flavus* and *Aspergillus fumigatus* was studied in immunocompromised mice (Alvarez et al., (2007) *J Infect* 55:68-74; Hoeben et al., (2006) *Antimicrob Agents Chemother.* 50:1552-1554). Single and multiple aerosolized dose studies in mice have demonstrated the ability to achieve effective anti-fungal pulmonary concentrations within 60 min after completion of nebulization while maintaining serum levels 25 to 50 times lower (McConville et al., (2006) *Pharm Res.* 23:901-911; Vaughn et al., (2006) *Eur J Pharm Biopharm.* 63:95-102).

Nevertheless, although these antifungal results appear promising in mice, the authors consistently cautioned that further studies are needed before extrapolating them to the clinical setting. Anti-fibrotic treatment generally lasts for months, or years, or even for life, while anti-fungal treatments last for at most a few weeks. Therefore, the concerns for any side effect of an anti-fibrotic drug is greatly exacerbated, and must be confronted.

Accordingly, in one embodiment, the present invention provides a dosage form for delivering itraconazole for treating IPF in a patient in need thereof, wherein the dosage form directly delivers an effective amount of itraconazole into the lungs of the patient. The dosage form can be a spray or a nebulizer, and delivers less than about $\frac{1}{10}$ of an oral dosage for to the patient.

In one embodiment, the dosage form further comprises a pharmaceutically effective amount of an antifibrosis agent, which can be pirfenidone or nintedanib.

DETAILED DESCRIPTION OF THE INVENTION

Figure 1:
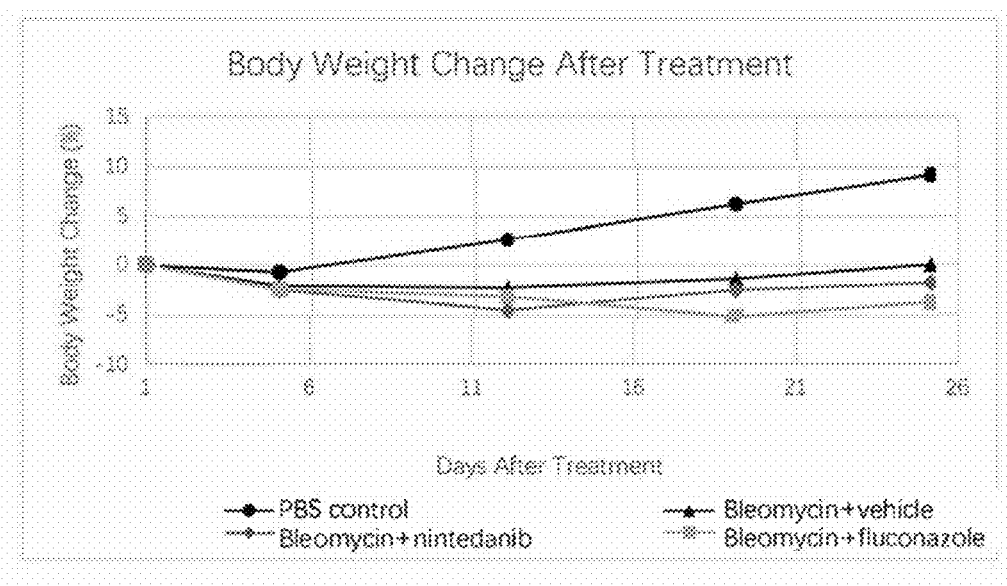
FIG. 1 shows mice body weight changes following bleomycin plus nintedanib or fluconazole treatment.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

The present invention relates to methods and compositions for treating IPF in humans. The terms "treat" and "treatment" are used broadly to denote therapeutic and prophylactic interventions that favorably alter a pathological state. Treatments include procedures that moderate or reverse the progression of, reduce the severity of, prevent, or cure a disease. As used herein, the term "IPF" or "idiopathic pulmonary fibrosis" includes all forms of idiopathic pulmonary fibrosis, such as occupational and environmental, autoimmune, scleroderma, sarcoidosis, drug- and radiation-induced, and genetic/familial fibrosis.

The amount of itraconazole administered can vary with the patient, the route of administration and the result sought. Optimum dosing regimens for particular patients can be readily determined by one skilled in the art. For example, the daily dose of itraconazole can be from about 20 mg to about 1200 mg. In one embodiment, the daily dose of itraconazole may be in the range of 0.5 milligrams per kilogram of body weight to 200 milligrams per kilogram of body weight.

According to a certain embodiment of the present invention, there is provided an itraconazole formulation composition for oral pulmonary or intranasal inhalation delivery, comprising formulations for aerosol administration of itraconazole for the prevention or treatment of idiopathic pulmonary fibrosis. According to a certain embodiment of the present invention, there is provided methods of administering itraconazole to a patient in need thereof, or a method for treating IPF of a patient in need thereof, comprising using the inhalation formulation of the present invention.

Itraconazole can be administered in the form of a pharmaceutical composition together with a pharmaceutical carrier. The pharmaceutical composition can be in dosage unit form such as powder, syrup, suspension, emulsion, solution, gel including hydrogel, spray or aerosol, or the like. Sustained release formulations can also be used.

A large variety of delivery vehicles for administering the composition are contemplated as within the scope of the present invention when containing therapeutic amounts of itraconazole. Suitable delivery vehicles include, but are not limited to, microcapsules or microspheres; liposomes and other lipid-based release systems; absorbable and/or biodegradable mechanical barriers, polymeric or gel-like materials.

In some embodiments, the dosage form may provide a dosage of between 20 to 1200 mg of itraconazole. The dosage form may also be formulated to provide a daily dosage in the range of 1-20 mg per kilogram of body weight.

The pharmaceutical compositions may be formulated according to conventional pharmaceutical practice. Sustained release formulations can also be used. Itraconazole may be formulated in a variety of ways that are known in the art, e.g. as liquid.

In accordance with the invention, the pharmaceutical composition of the present invention is an effective treatment for IPF and provides an effective means of delaying disease progression associated with fibrosis. The composition in inhaler, for example, can be more effective than an oral dosage, with fewer side effects. Lower doses can be used, reducing the overall side effect burden.

Inhalable Formulation/Aerosol Delivery

Itraconazole is preferably directly administered as an aerosol to a site of IPF pathology.

Several device technologies exist to deliver either dry powder or liquid aerosolized products. Dry powder formulations generally require less time for drug administration, yet longer and more expensive development efforts. Conversely, liquid formulations have historically suffered from longer administration times, yet have the advantage of shorter and less expensive development efforts.

The solubility of itraconazole in 0.1N HCl is approximately 4-6 μg/mL and in water is 1-4 ng/mL. Itraconazole exhibits very poor oral bioavailability owing to its insolubility in intestinal fluids.

Accordingly, in one embodiment, a particular formulation of itraconazole disclosed herein is combined with a particular aerosolizing device to provide an aerosol for inhalation that is optimized for maximum drug deposition at a desired site. Factors that can be optimized include solution or solid particle formulation, rate of delivery, and particle size and distribution produced by the aerosolizing device.

Particle Size and Distribution

The distribution of aerosol particle/droplet size can be expressed in terms of either: the mass median aerodynamic diameter (MMAD)—the droplet size at which half of the mass of the aerosol is contained in smaller droplets and half in larger droplets; volumetric mean diameter (VMD); mass median diameter (MMD); or the fine particle fraction (FPF)—the percentage of particles that are <5 μm in diameter. These measurements may be made by impaction (MMD and MMAD) or by laser (VMD). For liquid particles, VMD, MMD and MMAD may be the same if environmental conditions are maintained, e.g., standard humidity. However, if humidity is not maintained, MMD and MMAD determinations will be smaller than VMD due to dehydration during impactor measurements. For the purposes of this description, VMD, MMD and MMAD measurements are considered to be under standard conditions such that descriptions of VMD, MMD and MMAD will be comparable. Similarly, dry powder particle size determinations in MMD and MMAD are also considered comparable.

These measures have been used for comparisons of the in vitro performance of different inhaler device and drug combinations. In general, the higher the fine particle fraction, the higher the proportion of the emitted dose that is likely to deposit in the lung.

Generally, inhaled particles are subject to deposition by one of two mechanisms: impaction, which usually predominates for larger particles, and sedimentation, which is prevalent for smaller particles. Impaction occurs when the momentum of an inhaled particle is large enough that the particle does not follow the air stream and encounters a physiological surface. In contrast, sedimentation occurs primarily in the deep lung when very small particles which have traveled with the inhaled air stream encounter physiological surfaces as a result of random diffusion within the air stream.

For pulmonary administration, the upper airways are avoided in favor of the middle and lower airways. Pulmonary drug delivery may be accomplished by inhalation of an aerosol through the mouth and throat. Particles having a mass median aerodynamic diameter (MMAD) of greater than about 5 microns generally do not reach the lung; instead, they tend to impact the back of the throat and are swallowed and possibly orally absorbed. Particles having diameters of about 1 to about 5 microns are small enough to reach the upper- to mid-pulmonary region (conducting airways), but are too large to reach the alveoli. Smaller particles, i.e., about 0.5 to about 2 microns, are capable of reaching the alveolar region. Particles having diameters smaller than about 0.5 microns can also be deposited in the alveolar region by sedimentation, although very small particles may be exhaled.

In some embodiments, the particle size of the aerosol is optimized to maximize itraconazole deposition at the site of pulmonary pathology, and to maximize tolerability.

Intolerability (e.g., cough and bronchospasm) may occur from upper airway deposition from both inhalation impaction of large particles and settling of small particles during repeated inhalation and expiration. Thus, in one embodiment, an optimum particle size is used (e.g., MMAD=2-5 μm) in order to maximize deposition at a mid-lung and to minimize intolerability associated with upper airway deposition. Moreover, generation of a defined particle size with limited geometric standard deviation (GSD) may optimize deposition and tolerability. Narrow GSD limits the number of particles outside the desired MMAD size range.

In one embodiment, an aerosol containing itraconazole disclosed herein is provided having a MMAD from about 2 microns to about 5 microns with a GSD of less than or equal to about 2.5 microns. In another embodiment, an aerosol having an MMAD from about 2.8 microns to about 4.3 microns with a GSD less than or equal to 2 microns is provided. In another embodiment, an aerosol having an MMAD from about 2.5 microns to about 4.5 microns with a GSD less than or equal to 1.8 microns is provided.

In some embodiments, itraconazole that is intended for respiratory delivery can be administered as aqueous formulations, as suspensions or solutions in halogenated hydrocarbon propellants, or as dry powders. Aqueous formulations may be aerosolized by liquid nebulizers employing either hydraulic or ultrasonic atomization. Propellant-based systems may use suitable pressurized metered-dose inhalers (pMDIs). Dry powders may use dry powder inhaler devices (DPIs), which are capable of dispersing the drug substance effectively. A desired particle size and distribution may be obtained by choosing an appropriate device.

Lung Deposition as used herein, refers to the fraction of the nominal dose of an active pharmaceutical ingredient (API) that is bioavailable at a specific site of pharmacologic activity upon administration of the agent to a patient via a specific delivery route. For example, a lung deposition of 30% means 30% of the active ingredient in the inhalation device just prior to administration is deposited in the lung. Likewise, a lung deposition of 60% means 60% of the active ingredient in the inhalation device just prior to administration is deposited in the lung, and so forth. Lung deposition can be determined using methods of scintigraphy or deconvolution. In some embodiments, the present invention provides for methods and inhalation systems for the treatment or prophylaxis of a respiratory condition in a patient, comprising administering to the patient a nominal dose of itraconazole with a liquid nebulizer. In some embodiments, the liquid nebulizer is a high efficiency liquid nebulizer. In some embodiments, a lung deposition of itraconazole of at least about 7%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, or at least about 85%, based on the nominal dose of itraconazole is achieved.

There are two main methods used to measure aerosol deposition in the lungs. First, γ-scintigraphy is performed by radiolabeling the drug with a substance like 99m-technetium, and scanning the subject after inhalation of the drug. This technique has the advantage of being able to quantify the proportion of aerosol inhaled by the patient, as well as regional distribution in the upper airway and lungs. Second, since most of the drug deposited in the lower airways will be absorbed into the bloodstream, pharmacokinetic techniques are used to measure lung deposition. This technique can assess the total amount of ICSs that interacts with the airway epithelium and is absorbed systemically, but will miss the small portion that may be expectorated or swallowed after mucociliary clearance, and cannot tell us about regional distribution. Therefore, γ-scintigraphy and pharmacokinetic studies are in many cases considered complementary.

In some embodiments, administration of itraconazole with a liquid nebulizer provides a GSD of emitted droplet size distribution of about 1.0 μm to about 2.5 μm, about 1.2 μm to about 2.0 μm, or about 1.0 μm to about 2.0 μm. In some embodiments, the MMAD is about 0.5 μm to about 5 μm, or about 1 to about 4 μm or less than about 5 μm. In some embodiments, the VMD is about 0.5 μm to about 5 μm, or about 1 to about 4 μm or less than about 5 μm.

The Delivered Dose (DD) of drug to a patient is the certain portion of volume of liquid filled into the nebulizer, i.e. the fill volume, which is emitted from the mouthpiece of the device. The difference between the nominal dose and the DD is the amount of volume lost primarily to residues, i.e. the amount of fill volume remaining in the nebulizer after administration, or is lost in aerosol form during expiration of air from the patient and therefore not deposited in the patient's body. In some embodiments, the DD of the nebulized formulations described herein is at least about 30%, at least about 35%, at least about 40%, at least about 45%, at least about 50%, at least about 55%, at least about 60%, at least about 65%, at least about 70%, or at least about 80%.

The Respirable Delivered Dose (RDD) is an expression of the delivered mass of drug contained within emitted droplets from a nebulizer that are small enough to reach and deposit on the surface epithelium of the patients lung. The RDD is determined by multiplying the DD by the FPF.

In some embodiments, administration of an aqueous inhalation itraconazole solution with a liquid nebulizer provides an RDD of at least about 30%, at least about 35%, at least about 40%, at least about 45%, at least about 50%, at least about 55%, at least about 60%, at least about 65%, at least about 70%, at least about 75%, or at least about 80%.

In one embodiment, described herein is an aqueous droplet containing itraconaxole, wherein the aqueous droplet has a diameter less than about 5.0 μm. In some embodiments, the aqueous droplet has a diameter less than about 5.0 μm, less than about 4.5 μm, less than about 4.0 μm, less than about 3.5 μm, less than about 3.0 μm, less than about 2.5 μm, less than about 2.0 μm, less than about 1.5 μm, or less than about 1.0 μm.

In some embodiments, the aqueous droplet further comprises one or more co-solvents. In some embodiments, the one or more co-solvents are selected from ethanol and propylene glycol. In some embodiments, the aqueous droplet further comprises a buffer. In some embodiments, the buffer is a citrate buffer or a phosphate buffer. In some embodiments, the droplet was produced from a liquid nebulizer and an aqueous solution of itraconazole as described herein. In some embodiments, the aqueous droplet is produced from an aqueous solution that has concentration of itraconazole between about 0.1 mg/mL and about 60 mg/mL.

Also described are aqueous aerosols comprising a plurality of aqueous droplets of itraconazole as described herein.

In some embodiments, at least about 30% of the aqueous droplets in the aerosol have a diameter less than about 5 μm. In some embodiments, at least about 35%, at least about 40%, at least about 45%, at least about 50%, at least about 55%, at least about 60%, at least about 65%, at least about 70%, at least about 75%, at least about 80%, at least about 85%, or at least about 90% of the aqueous droplets in the aerosol have a diameter less than about 5 μm. In some embodiments, the aqueous aerosols are produced with a liquid nebulizer. In some embodiments, the aqueous aerosols are produced with a high efficiency liquid nebulizer.

Liquid Nebulizer

In one embodiment, a nebulizer is selected on the basis of allowing the formation of an aerosol of an itraconazole disclosed herein having an MMAD predominantly between about 1 to about 5 microns. In one embodiment, the delivered amount of itraconazole provides a therapeutic effect for IPF pathology.

Two types of nebulizers, jet and ultrasonic, are able to produce and deliver aerosol particles having sizes between 2 and 4 micron. These particle sizes have been shown as being optimal for middle airway deposition. However, unless a specially formulated solution is used, these nebulizers typically need larger volumes to administer sufficient amount of drug to obtain a therapeutic effect. A jet nebulizer utilizes air pressure breakage of an aqueous solution into aerosol droplets. An ultrasonic nebulizer utilizes shearing of the aqueous solution by a piezoelectric crystal. Typically, however, the jet nebulizers are only about 10% efficient under clinical conditions, while the ultrasonic nebulizer is only about 5% efficient. The amount of pharmaceutical deposited and absorbed in the lungs is thus a fraction of the 10% in spite of the large amounts of the drug placed in the nebulizer. The amount of drug that is placed in the nebulizer prior to administration to the mammal is generally referred to the "nominal dose," or "loaded dose." The volume of solution containing the nominal dose is referred to as the "fill volume." Smaller particle sizes or slow inhalation rates permit deep lung deposition. Both middle-lung and alveolar deposition may be desired for this invention depending on the indication, e.g., middle and/or alveolar deposition for pulmonary fibrosis and systemic delivery. Exemplary disclosure of compositions and methods for formulation delivery using nebulizers can be found in, e.g., US 2006/0276483, including descriptions of techniques, protocols and characterization of aerosolized mist delivery using a vibrating mesh nebulizer.

Accordingly, in one embodiment, a vibrating mesh nebulizer is used to deliver in preferred embodiments an aerosol of itraconazole as disclosed herein. A vibrating mesh nebulizer comprises a liquid storage container in fluid contact with a diaphragm and inhalation and exhalation valves. In one embodiment, about 1 to about 6 mL of itraconazole formulation is placed in the storage container and the aerosol generator is engaged producing atomized aerosol of particle sizes selectively between about 1 and about 5 micron. In one embodiment, about 1 to about 10 mL of itraconazole formulation is placed in the storage container and the aerosol generator is engaged producing atomized aerosol of particle sizes selectively between about 1 and about 5 micron. In one embodiment, about the volume of itraconazole formulation that is originally placed in the storage container and the aerosol generator is replaced to increase the administered dose size.

In some embodiments, an itraconazole formulation as disclosed herein, is placed in a liquid nebulization inhaler and prepared in dosages to deliver from about 34 mg to about 463 mg from a dosing solution of about 0.5 to about 6 mL with MMAD particles sizes between about 1 to about 5 micron being produced.

By non-limiting example, a nebulized itraconazole may be administered in the described respirable delivered dose in less than about 20 min, less than about 15 min, less than about 10 min, less than about 7 min, less than about 5 min, less than about 3 min, or less than about 2 min.

By non-limiting example, a nebulized itraconazole may be administered in the described respirable delivered dose using a breath-actuated nebulizer in less than about 20 min, less than about 10 min, less than about 7 min, less than about 5 min, less than about 3 min, or less than about 2 min.

By non-limiting example, in other circumstances, a nebulized itraconazole may achieve improved tolerability and/or exhibit an area-under-the-curve (AUC) shape-enhancing characteristic when administered over longer periods of time. Under these conditions, the described respirable delivered dose in more than about 2 min, preferably more than about 3 min, more preferably more than about 5 min, more preferably more than about 7 min, more preferably more than about 10 min, and in some cases most preferable from about 10 to about 20 min.

In one embodiment, itraconazole is formulated to permit mist, gas-liquid suspension or liquid nebulized, dry powder and/or metered-dose inhaled aerosol administration to supply effective concentrations or amounts conferring desired anti-fibrotic or tissue-remodeling benefits, for instance, to prevent, manage or treat patients with pulmonary fibrosis.

Any known inhalation nebulizer suitable to provide delivery of a medicament as described herein may be used in the various embodiments and methods described herein. Such nebulizers include, e.g., jet nebulizers, ultrasonic nebulizers, pulsating membrane nebulizers, nebulizers with a vibrating mesh or plate with multiple apertures, and nebulizers comprising a vibration generator and an aqueous chamber. Examples of commercially available nebulizers suitable for use in the present invention are described, inter alia, in U.S. Pat. No. 10,105,356, which is incorporated herein by reference in its entirety.

In one aspect, described herein is a method for the treatment of idiopathic pulmonary fibrosis in a mammal comprising administering a dose of itraconazole by inhalation to the mammal in need thereof on a chronic dosing schedule. In some embodiments, the continuous dosing schedule includes administering a dose of itraconazole daily, every other day, every third day, every fourth day, every fifth day, every sixth day, weekly, biweekly, monthly or bimonthly. In some embodiments, the dosing schedule, whether daily or less than daily, includes administering one, two, three, or more than three doses of itraconazole on the days of dosing.

In some embodiments, each inhaled dose of itraconazole is administered with a nebulizer, a metered dose inhaler, or a dry powder inhaler. In some embodiments, each inhaled dose comprises a solution, e.g. an aqueous solution, and/or an ethanol solution of itraconazole. In some embodiments, each inhaled dose comprises from about 0.4 mL to about 240 mL of an aqueous solution of itraconazole, wherein the concentration of itraconazole in the aqueous solution is from about 0.1 mg/mL to about 60 mg/mL, such as 5 mg/mL to 50 mg/mL.

In some embodiments, the solution of each inhaled dose further comprises one or more additional ingredients selected from co-solvents, tonicity agents, sweeteners, surfactants, wetting agents, chelating agents, anti-oxidants, salts, and buffers. In some embodiments, the aqueous solution of each inhaled dose may further comprise ethanol, a citrate buffer or phosphate buffer, and one or more salts selected from the group consisting of sodium chloride, magnesium chloride, sodium bromide, magnesium bromide, calcium chloride and calcium bromide.

In some embodiments, the aqueous solution of each inhaled dose comprises: water, ethanol, sodium carboxymethyl cellulose, or DMSO/PEG400; itraconazole at a concentration from about 5 mg/mL to about 50 mg/mL; one or more salts, wherein the total amount of the one or more salts is from about 0.01% to about 2.0% by weight of the weight of aqueous solution; and optionally a phosphate buffer that maintains the pH of the solution from about pH 5.0 to about pH 8.0, or citrate buffer than maintains the pH of the solution from about 4.0 to about 7.0.

In some embodiments, each inhaled dose is administered with a liquid nebulizer. In some embodiments, the inhaled doses are delivered by nebulization using standard tidal breathing of continuous flow aerosol or breath actuated aerosol.

In some embodiments, the liquid nebulizer: (i) after administration of the inhaled dose, achieves lung deposition of at least 7% of the itraconazole administered to the mammal; (ii) provides a Geometric Standard Deviation (GSD) of emitted droplet size distribution of the aqueous solution of about 1.0 μm to about 2.5 μm; (iii) provides: a) a mass median aerodynamic diameter (MMAD) of droplet size of the aqueous solution emitted with the high efficiency liquid nebulizer of about 1 μm to about 5 μm; b) a volumetric mean diameter (VMD) of about 1 μm to about 5 μm; and/or c) a mass median diameter (MMD) of about 1 μm to about 5 μm; or (iv) provides a fine particle fraction (FPF=% 55 μm) of droplets emitted from the liquid nebulizer of at least about 30%. In some embodiments, the liquid nebulizer provides an output rate of at least 0.1 mL/min; or provides at least about 25% of the aqueous solution to the mammal.

In some embodiments, a) the lung tissue Cmax of itraconazole from each inhaled dose is at least equivalent to or greater than a lung tissue Cmax of up to 801 mg of an orally administered dosage of itraconazole; and/or b) the blood AUG-24 of itraconazole from each inhaled dose that is directly administered to the lungs of the mammal is less than or equivalent to the blood AUG-24 of up to 801 mg of an orally administered dosage of itraconazole. In some embodiments, the blood AUG-24 of itraconazole from each inhaled dose is less than the blood AUG-24 of up to 801 mg of an orally administered dosage of itraconazole. In some embodiments, the blood AUG-24 of itraconazole from each inhaled dose is less than 80%, less than 70%, less than 60%, less than 50%, less than 40%, less than 30%, less than 20%, less than 10%, less than 5%, less than 2.5%, less than 1.0%, less than 0.5%, less than 0.25%, less than 0.1%, less than 0.05%, less than 0.025% or less than 0.01% of the blood AUG-24 of up to 801 mg of an orally administered dosage of itraconazole. In some embodiments, the blood AUG-24 of itraconazole from each inhaled dose is between 0.01-90%, 0.01-80%, 0.01-70%, 0.01-60%, 0.01-50%, 0.01-40%, 0.01-30%, 0.01-20%, 0.01-10%, 0.01-5%, 0.01-2.5%, 0.01-1%, 0.01-0.1%, 5-90%, between 5-80%, between 5-70%, between 5-60%, between 5-50%, between 5-40%, between 5-30%, between 5-20%, between 5-10%, between 1-5%, between 1-10%, between 1-20%, between 1-30%, between 1-40%, between 1-50%, between 1-60%, between 1-70%, between 1-80%, or between 1-90% of the blood AUG-24 of up to 801 mg of an orally administered dosage of itraconalzole. In some embodiments, wherein each inhaled dose is less than ½ of the up to 801 mg of an orally administered dosage of itraconazole. In some embodiments, wherein each inhaled dose is less than ½, ⅓, ¼, ⅕, ⅙, ⅛, 1/10, 1/20, 1/40, 1/50, 1/75, 1/100, 1/200, 1/300, or 1/400 of the up to 801 mg of an orally administered dosage of itraconazole.

Nanoparticulate Compositions

Another embodiment is directed to dry powders which contain nanoparticulate compositions for pulmonary or nasal delivery. The powders may consist of respirable aggregates of nanoparticulate drug particles, or of respirable particles of a diluent which contains at least one embedded drug nanoparticle. Powders containing nanoparticulate drug particles can be prepared from aqueous dispersions of nanoparticles by removing the water via spray-drying or lyophilization (freeze drying). Spray-drying is less time consuming and less expensive than freeze-drying, and therefore more cost-effective. However, certain drugs, such as biologicals benefit from lyophilization rather than spray-drying in making dry powder formulations.

Conventional micronized drug particles used in dry powder aerosol delivery having particle diameters of from about 1 to about 5 microns MMAD are often difficult to meter and disperse in small quantities because of the electrostatic cohesive forces inherent in such powders. These difficulties can lead to loss of drug substance to the delivery device as well as incomplete powder dispersion and sub-optimal delivery to the lung. Many drug compounds, particularly proteins and peptides, are intended for deep lung delivery and systemic absorption. Since the average particle sizes of conventionally prepared dry powders are usually in the range of from about 1 to about 5 microns MMAD, the fraction of material which actually reaches the alveolar region may be quite small. Thus, delivery of micronized dry powders to the lung, especially the alveolar region, is generally very inefficient because of the properties of the powders themselves.

The dry powder aerosols which contain nanoparticulate drugs can be made smaller than comparable micronized drug substance and, therefore, are appropriate for efficient delivery to the deep lung. Moreover, aggregates of nanoparticulate drugs are spherical in geometry and have good flow properties, thereby aiding in dose metering and deposition of the administered composition in the lung or nasal cavities.

Dry nanoparticulate compositions can be used in both DPIs and pMDIs. As used herein, "dry" refers to a composition having less than about 5% water.

In one embodiment, compositions are provided containing nanoparticles which have an effective average particle size of less than about 1000 nm, more preferably less than about 400 nm, less than about 300 nm, less than about 250 nm, or less than about 200 nm, as measured by light-scattering methods. By "an effective average particle size of less than about 1000 nm" it is meant that at least 50% of the drug particles have a weight average particle size of less than about 1000 nm when measured by light scattering techniques. Preferably, at least 70% of the drug particles have an average particle size of less than about 1000 nm, more preferably at least 90% of the drug particles have an average particle size of less than about 1000 nm, and even more preferably at least about 95% of the particles have a weight average particle size of less than about 1000 nm.

For aqueous aerosol formulations, the nanoparticulate itraconazole may be present at a concentration of about 34 mg/mL up to about 463 mg/mL. For dry powder aerosol formulations, the nanoparticulate agent may be present at a concentration of about 34 mg/g up to about 463 mg/g, depending on the desired drug dosage. Concentrated nanoparticulate aerosols, defined as containing a nanoparticulate drug at a concentration of about 34 mcg/mL up to about 463 mg/mL for aqueous aerosol formulations, and about 34 mg/g up to about 463 mg/g for dry powder aerosol formulations, are specifically provided. Such formulations provide effective delivery to appropriate areas of the lung or nasal cavities in short administration times, i.e., less than about 3-15 seconds per dose as compared to administration times of up to 4 to 20 minutes as found in conventional pulmonary nebulizer therapies.

Nanoparticulate drug compositions for aerosol administration can be made by, for example, (1) nebulizing a dispersion of a nanoparticulate drug, obtained by either grinding or precipitation; (2) aerosolizing a dry powder of aggregates of nanoparticulate drug and surface modifier (the aerosolized composition may additionally contain a diluent); or (3) aerosolizing a suspension of nanoparticulate drug or drug aggregates in a non-aqueous propellant. The aggregates of nanoparticulate drug and surface modifier, which may additionally contain a diluent, can be made in a non-pressurized or a pressurized non-aqueous system. Concentrated aerosol formulations may also be made via such methods.

Milling of aqueous drug to obtain nanoparticulate drug may be performed by dispersing drug particles in a liquid dispersion medium and applying mechanical means in the presence of grinding media to reduce the particle size of the drug to the desired effective average particle size. The particles can be reduced in size in the presence of one or more surface modifiers. Alternatively, the particles can be contacted with one or more surface modifiers after attrition. Other compounds, such as a diluent, can be added to the drug/surface modifier composition during the size reduction process. Dispersions can be manufactured continuously or in a batch mode.

Another method of forming nanoparticle dispersion is by microprecipitation. This is a method of preparing stable dispersions of drugs in the presence of one or more surface modifiers and one or more colloid stability enhancing surface active agents free of any trace toxic solvents or solubilized heavy metal impurities. Such a method comprises, for example, (1) dissolving the drug in a suitable solvent with mixing; (2) adding the formulation from step (1) with mixing to a solution comprising at least one surface modifier to form a clear solution; and (3) precipitating the formulation from step (2) with mixing using an appropriate nonsolvent. The method can be followed by removal of any formed salt, if present, by dialysis or diafiltration and concentration of the dispersion by conventional means. The resultant nanoparticulate drug dispersion can be utilized in liquid nebulizers or processed to form a dry powder for use in a DPI or pMDI.

In a non-aqueous, non-pressurized milling system, a non-aqueous liquid having a vapor pressure of about 1 atm or less at room temperature and in which the drug substance is essentially insoluble may be used as a wet milling medium to make a nanoparticulate drug composition. In such a process, a slurry of drug and surface modifier may be milled in the non-aqueous medium to generate nanoparticulate drug particles. Examples of suitable non-aqueous media include ethanol, trichloromonofluoromethane, (CFC-11), and dichlorotetafluoroethane (CFC-114). An advantage of using CFC-11 is that it can be handled at only marginally cool room temperatures, whereas CFC-114 requires more controlled conditions to avoid evaporation. Upon completion of milling the liquid medium may be removed and recovered under vacuum or heating, resulting in a dry nanoparticulate composition. The dry composition may then be filled into a suitable container and charged with a final propellant. Exemplary final product propellants, which ideally do not contain chlorinated hydrocarbons, include HFA-134a (tetrafluoroethane) and HFA-227 (heptafluoropropane). While non-chlorinated propellants may be preferred for environmental reasons, chlorinated propellants may also be used in this embodiment of the invention.

In a non-aqueous, pressurized milling system, a non-aqueous liquid medium having a vapor pressure significantly greater than 1 atm at room temperature may be used in the milling process to make nanoparticulate drug compositions. If the milling medium is a suitable halogenated hydrocarbon propellant, the resultant dispersion may be filled directly into a suitable pMDI container. Alternately, the milling medium can be removed and recovered under vacuum or heating to yield a dry nanoparticulate composition. This composition can then be filled into an appropriate container and charged with a suitable propellant for use in a pMDI.

Spray drying is a process used to obtain a powder containing nanoparticulate drug particles following particle size reduction of the drug in a liquid medium. In general, spray-drying may be used when the liquid medium has a vapor pressure of less than about 1 atm at room temperature. A spray-dryer is a device which allows for liquid evaporation and drug powder collection. A liquid sample, either a solution or suspension, is fed into a spray nozzle. The nozzle generates droplets of the sample within a range of about 20 to about 100 micron in diameter which are then transported by a carrier gas into a drying chamber. The carrier gas temperature is typically from about 80 to about 200° C. The droplets are subjected to rapid liquid evaporation, leaving behind dry particles which are collected in a special reservoir beneath a cyclone apparatus. Smaller particles in the range down about 1 micron to about 5 microns are also possible.

If the liquid sample consists of an aqueous dispersion of nanoparticles and surface modifier, the collected product will consist of spherical aggregates of the nanoparticulate drug particles. If the liquid sample consists of an aqueous dispersion of nanoparticles in which an inert diluent material was dissolved (such as lactose or mannitol), the collected product will consist of diluent (e.g., lactose or mannitol) particles which contain embedded nanoparticulate drug particles. The final size of the collected product can be controlled and depends on the concentration of nanoparticulate drug and/or diluent in the liquid sample, as well as the droplet size produced by the spray-dryer nozzle. Collected products may be used in conventional DPIs for pulmonary or nasal delivery, dispersed in propellants for use in pMDIs, or the particles may be reconstituted in water for use in nebulizers.

In some instances it may be desirable to add an inert carrier to the spray-dried material to improve the metering properties of the final product. This may especially be the case when the spray dried powder is very small (less than about 5 micron) or when the intended dose is extremely small, whereby dose metering becomes difficult. In general, such carrier particles (also known as bulking agents) are too large to be delivered to the lung and simply impact the mouth and throat and are swallowed. Such carriers typically consist of sugars such as lactose, mannitol, or trehalose. Other inert materials, including polysaccharides and cellulosics, may also be useful as carriers.

Spray-dried powders containing nanoparticulate drug particles may used in conventional DPIs, dispersed in propellants for use in pMDIs, or reconstituted in a liquid medium for use with nebulizers.

To avoid denaturization or destabilization by heat, sublimation is preferred over evaporation to obtain a dry powder nanoparticulate drug composition. This is because sublimation avoids the high process temperatures associated with spray-drying. In addition, sublimation, also known as freeze-drying or lyophilization, can increase the shelf stability of drug compounds, particularly for biological products. Freeze-dried particles can also be reconstituted and used in nebulizers. Aggregates of freeze-dried nanoparticulate drug particles can be blended with either dry powder intermediates or used alone in DPIs and pMDIs for either nasal or pulmonary delivery.

Sublimation involves freezing the product and subjecting the sample to strong vacuum conditions. This allows for the formed ice to be transformed directly from a solid state to a vapor state. Such a process is highly efficient and, therefore, provides greater yields than spray-drying. The resultant freeze-dried product contains drug and modifier(s). The drug is typically present in an aggregated state and can be used for inhalation alone (either pulmonary or nasal), in conjunction with diluent materials (lactose, mannitol, etc.), in DPIs or pMDIs, or reconstituted for use in a nebulizer.

Liposomal Compositions

In some embodiments, itraconazole may be formulated into liposome particles, which can then be aerosolized for inhaled delivery. Lipids which are useful in the present invention can be any of a variety of lipids including both neutral lipids and charged lipids. Carrier systems having desirable properties can be prepared using appropriate combinations of lipids, targeting groups and circulation enhancers. Additionally, the compositions provided herein can be in the form of liposomes or lipid particles, preferably lipid particles. As used herein, the term "lipid particle" refers to a lipid bilayer carrier which "coats" a nucleic acid and has little or no aqueous interior. More particularly, the term is used to describe a self-assembling lipid bilayer carrier in which a portion of the interior layer comprises cationic lipids which form ionic bonds or ion-pairs with negative charges on the nucleic acid (e.g., a plasmid phosphodiester backbone). The interior layer can also comprise neutral or fusogenic lipids and, in some embodiments, negatively charged lipids. The outer layer of the particle will typically comprise mixtures of lipids oriented in a tail-to-tail fashion (as in liposomes) with the hydrophobic tails of the interior layer. The polar head groups present on the lipids of the outer layer will form the external surface of the particle.

Liposomal bioactive agents can be designed to have a sustained therapeutic effect or lower toxicity allowing less frequent administration and an enhanced therapeutic index. Liposomes are composed of bilayers that entrap the desired pharmaceutical. These can be configured as multilamellar vesicles of concentric bilayers with the pharmaceutical trapped within either the lipid of the different layers or the aqueous space between the layers.

By non-limiting example, lipids used in the compositions may be synthetic, semi-synthetic or naturally-occurring lipids, including phospholipids, tocopherols, steroids, fatty acids, glycoproteins such as albumin, negatively-charged lipids and cationic lipids. Phosholipids include egg phosphatidylcholine (EPC), egg phosphatidylglycerol (EPG), egg phosphatidylinositol (EPI), egg phosphatidylserine (EPS), phosphatidylethanolamine (EPE), and egg phosphatidic acid (EPA); the soya counterparts, soy phosphatidylcholine (SPC); SPG, SPS, SPI, SPE, and SPA; the hydrogenated egg and soya counterparts (e.g., HEPC, HSPC), other phospholipids made up of ester linkages of fatty acids in the 2 and 3 of glycerol positions containing chains of 12 to 26 carbon atoms and different head groups in the 1 position of glycerol that include choline, glycerol, inositol, serine, ethanolamine, as well as the corresponding phosphatidic acids. The chains on these fatty acids can be saturated or unsaturated, and the phospholipid can be made up of fatty acids of different chain lengths and different degrees of unsaturation. In particular, the compositions of the formulations can include dipalmitoylphosphatidylcholine (DPPC), a major constituent of naturally-occurring lung surfactant as well as dioleoylphosphatidylcholine (DOPC) and dioleoylphosphatidylglycerol (DOPG). Other examples include dimyristoylphosphatidycholine (DMPC) and dimyristoylphosphatidylglycerol (DMPG) dipalmitoylphosphatidcholine (DPPC) and dipalmitoylphosphatidylglycerol (DPPG) distearoylphosphatidylcholine (DSPC) and distearoylphosphatidylglycerol (DSPG), dioleylphosphatidylethanolamine (DOPE) and mixed phospholipids like palmitoylstearoylphosphatidylcholine (PSPC) and palmitoylstearoylphosphatidylglycerol (PSPG), and single acylated phospholipids like mono-oleoyl-phosphatidylethanolamine (MOPE).

In a preferred embodiment, PEG-modified lipids are incorporated into the compositions of the present invention as the aggregation-preventing agent. The use of a PEG-modified lipid positions bulky PEG groups on the surface of the liposome or lipid carrier and prevents binding of DNA to the outside of the carrier (thereby inhibiting cross-linking and aggregation of the lipid carrier). The use of a PEG-ceramide is often preferred and has the additional advantages of stabilizing membrane bilayers and lengthening circulation lifetimes. Additionally, PEG-ceramides can be prepared with different lipid tail lengths to control the lifetime of the PEG-ceramide in the lipid bilayer. In this manner, "programmable" release can be accomplished which results in the control of lipid carrier fusion. For example, PEG-ceramides having C20-acyl groups attached to the ceramide moiety will diffuse out of a lipid bilayer carrier with a half-life of 22 hours. PEG-ceramides having C14- and C8-acyl groups will diffuse out of the same carrier with half-lives of 10 minutes and less than 1 minute, respectively. As a result, selection of lipid tail length provides a composition in which the bilayer becomes destabilized (and thus fusogenic) at a known rate. Though less preferred, other PEG-lipids or lipid-polyoxyethylene conjugates are useful in the present compositions. Examples of suitable PEG-modified lipids include PEG-modified phosphatidylethanolamine and phosphatidic acid, PEG-modified diacylglycerols and dialkylglycerols, PEG-modified dialkylamines and PEG-modified 1,2-diacyloxypropan-3-amines. Particularly preferred are PEG-ceramide conjugates (e.g., PEG-Cer-C8, PEG-Cer-C14 or PEG-Cer-C20) which are described in U.S. Pat. No. 5,820,873, incorporated herein by reference.

The compositions of the present invention can be prepared to provide liposome compositions which are about 50 nm to about 400 nm in diameter. One with skill in the art will understand that the size of the compositions can be larger or smaller depending upon the volume which is encapsulated. Thus, for larger volumes, the size distribution will typically be from about 80 nm to about 300 nm.

Surface Modifiers

Itraconazole may be prepared in a pharmaceutical composition with suitable surface modifiers which may be selected from known organic and inorganic pharmaceutical excipients. Such excipients include low molecular weight oligomers, polymers, surfactants and natural products. Preferred surface modifiers include nonionic and ionic surfactants. Two or more surface modifiers can be used in combination.

Representative examples of surface modifiers include cetyl pyridinium chloride, gelatin, casein, lecithin (phosphatides), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens™, such as e.g., Tween 20™, and Tween 80™, (ICI Specialty Chemicals)); polyethylene glycols (e.g., Carbowaxs 3350™, and 1450™, and Carbopol 934™, (Union Carbide)), dodecyl trimethyl ammonium bromide, polyoxyethylenestearates, colloidal silicon dioxide, phosphates, sodium dodecylsulfate, carboxymethylcellulose calcium, hydroxypropyl cellulose (HPC, HPC-SL, and HPC-L), hydroxypropyl methylcellulose (HPMC), carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), polyvinylpyrrolidone (PVP), 4-(1,1,3,3-tetaamethylbutyl)-phenol polymer with ethylene oxide and formaldehyde (also known as tyloxapol, superione, and triton), poloxamers (e.g., Pluronics F68™, and F108™, which are block copolymers of ethylene oxide and propylene oxide); poloxamines (e.g., Tetronic 908™, also known as Poloxamine 908™, which is a tetrafunctional block copolymer derived from sequential addition of propylene oxide and ethylene oxide to ethylene-diamine (BASF Wyandotte Corporation, Parsippany, N.J.)); a charged phospholipid such as dimyristoyl phophatidyl glycerol, dioctylsulfosuccinate (DOSS); Tetronic 1508™; (T-1508) (BASF Wyandotte Corporation), dialkylesters of sodium sulfosuccinic acid (e.g., Aerosol OT™, which is a dioctyl ester of sodium sulfosuccinic acid (American Cyana-mid)); Duponol P™, which is a sodium lauryl sulfate (DuPont); Tritons X-200™, which is an alkyl aryl polyether sulfonate (Rohm and Haas); Crodestas F-110™, which is a mixture of sucrose stearate and sucrose distearate (Croda Inc.); p-isononylphenoxypoly-(glycidol), also known as Olin-Log™, or Surfactant 10-G™, (Olin Chemicals, Stam-ford, Conn.); Crodestas SL-40™, (Croda, Inc.); and SA9OHCO, which is C.sub.18H.sub.37CH.sub.2 (CON (CH.sub.3)—CH.sub.2(CHOH).sub.4(CH.sub.20H).sub.2 (Eastman Kodak Co.); decanoyl-N-methylglucamide; n-decyl.beta.-D-glucopyranoside; n-decyl.beta.-D-maltopy-ranoside; n-dodecyl.beta.-D-glucopyranoside; n-dodecyl-.beta.-D-maltoside; heptanoyl-N-methylglucamide; n-hep-tyl-.beta.-D-glucopyranoside; n-heptyl.beta.-D-thioglucoside; n-hexyl.beta.-D-glucopyranoside; nonanoyl-N-methylglucamide; n-noyl.beta.-D-glucopyranoside; octanoyl-N-methylglucamide; n-octyl-.beta.-D-glucopyra-noside; octyl.beta.-D-thioglucopyranoside; and the like. Tyloxapol is a particularly preferred surface modifier for the pulmonary or intranasal delivery of steroids, even more so for nebulization therapies.

Examples of surfactants for use in the solutions disclosed herein include, but are not limited to, ammonium laureth sulfate, cetamine oxide, cetrimonium chloride, cetyl alcohol, cetyl myristate, cetyl palmitate, cocamide DEA, cocami-dopropyl betaine, cocamidopropylamine oxide, cocamide MEA, DEA lauryl sulfate, di-stearyl phthalic acid amide, dicetyl dimethyl ammonium chloride, dipalmitoylethyl hydroxethylmonium, disodium laureth sulfosuccinate, di(hydrogenated) tallow phthalic acid, glyceryl dilaurate, glyceryl distearate, glyceryl oleate, glyceryl stearate, iso-propyl myristate nf, isopropyl palmitate nf, lauramide DEA, lauramide MEA, lauramide oxide, myristamine oxide, octyl isononanoate, octyl palmitate, octyldodecyl neopentanoate, olealkonium chloride, PEG-2 stearate, PEG-32 glyceryl caprylate/caprate, PEG-32 glyceryl stearate, PEG-4 and PEG-150 stearate & distearate, PEG-4 to PEG-150 laurate & dilaurate, PEG-4 to PEG-150 oleate & dioleate, PEG-7 glyceryl cocoate, PEG-8 beeswax, propylene glycol stearate, sodium C14-16 olefin sulfonate, sodium lauryl sulfoacetate, sodium lauryl sulphate, sodium trideceth sulfate, stearalko-nium chloride, stearamide oxide, TEA-dodecylbenzene sulfonate, TEA lauryl sulfate.

Most of these surface modifiers are known pharmaceuti-cal excipients and are described in detail in the Handbook of Pharmaceutical Excipients, published jointly by the Ameri-can Pharmaceutical Association and The Pharmaceutical Society of Great Britain (The Pharmaceutical Press, 1986), specifically incorporated by reference. The surface modifiers are commercially available and/or can be prepared by tech-niques known in the art. The relative amount of drug and surface modifier can vary widely and the optimal amount of the surface modifier can depend upon, for example, the particular drug and surface modifier selected, the critical micelle concentration of the surface modifier if it forms micelles, the hydrophilic-lipophilic-balance (HLB) of the surface modifier, the melting point of the surface modifier, the water solubility of the surface modifier and/or drug, the surface tension of water solutions of the surface modifier, etc.

In the present invention, the optimal ratio of drug to surface modifier is about 0.1% to about 99.9% itraconazole, more preferably about 10% to about 90%.

Microspheres

Microspheres can be used for pulmonary delivery of itraconazole by first adding an appropriate amount of drug compound to be solubilized in water. For example, an aqueous itraconazole solution may be dispersed in methyl-ene chloride containing a predetermined amount (0.1-1% w/v) of poly(DL-lactide-co-glycolide) (PLGA) by probe sonication for 1-3 min on an ice bath. Separately, an itra-conazole may be solubilized in methylene chloride contain-ing PLGA (0.1-1% w/v). The resulting water-in-oil primary emulsion or the polymer/drug solution will be dispersed in an aqueous continuous phase consisting of 1-2% polyvinyl alcohol (previously cooled to 4° C.) by probe sonication for 3-5 min on an ice bath. The resulting emulsion will be stirred continuously for 2-4 hours at room temperature to evaporate methylene chloride. Microparticles thus formed will be separated from the continuous phase by centrifuging at 8000-10000 rpm for 5-10 min. Sedimented particles will be washed thrice with distilled water and freeze dried. Freeze-dried itraconazole microparticles will be stored at −20° C.

By non-limiting example, a spray drying approach will be employed to prepare itraconazole microspheres. An appro-priate amount of itraconazole will be solubilized in meth-ylene chloride containing PLGA (0.1-1%). This solution will be spray dried to obtain the microspheres.

By non-limiting example, itraconazole microparticles will be characterized for size distribution (requirement: 90%<5 μm, 95%<10 μm), shape, drug loading efficiency and drug release using appropriate techniques and methods.

By non-limiting example, this approach may also be used to sequester and improve the water solubility of solid, AUC shape-enhancing formulations.

A certain amount of itraconazole can be first dissolved in the minimal quantity of ethanol 96% necessary to maintain the fluoroquinolone in solution when diluted with water from 96 to 75%. This solution can then be diluted with water to obtain a 75% ethanol solution and then a certain amount of paracetamol can be added to obtain the following w/w drug/polymer ratios: 1:2, 1:1, 2:1, 3:1, 4:1, 6:1, 9:1, and 19:1. These final solutions are spray-dried under the follow-ing conditions: feed rate, 15 mL/min; inlet temperature, 110° C.; outlet temperature, 85° C.; pressure 4 bar and throughput of drying air, 35 m3/hr. Powder is then collected and stored under vacuum in a desiccator.

Solid Lipid Particles

Preparation of itraconazole solid lipid particles may involve dissolving the drug in a lipid melt (phospholipids such as phophatidyl choline and phosphatidyl serine) main-tained at least at the melting temperature of the lipid, followed by dispersion of the drug-containing melt in a hot aqueous surfactant solution (typically 1-5% w/v) maintained at least at the melting temperature of the lipid. The coarse dispersion will be homogenized for 1-10 min using a Micro-fluidizer® to obtain a nanoemulsion. Cooling the nanoemul-sion to a temperature between 4-25° C. will re-solidify the lipid, leading to formation of solid lipid nanoparticles. Optimization of formulation parameters (type of lipid matrix, surfactant concentration and production parameters) will be performed so as to achieve a prolonged drug deliv-ery. By non-limiting example, this approach may also be used to sequester and improve the water solubility of solid, AUC shape-enhancing formulations for nanoparticle-based formulations.

Melt-Extrusion AUC Shape-Enhancing Formulation

Melt-Extrusion AUC shape-enhancing itraconazole formulations may be preparation by dissolving the drugs in micelles by adding surfactants or preparing micro-emulsion, forming inclusion complexes with other molecules such as cyclodextrins, forming nanoparticles of the drugs, or embedding the amorphous drugs in a polymer matrix. Embedding the drug homogeneously in a polymer matrix produces a solid dispersion. Solid dispersions can be prepared in two ways: the solvent method and the hot melt method. The solvent method uses an organic solvent wherein the drug and appropriate polymer are dissolved and then (spray) dried. The major drawbacks of this method are the use of organic solvents and the batch mode production process. The hot melt method uses heat in order to disperse or dissolve the drug in an appropriate polymer. The melt-extrusion process is an optimized version of the hot melt method. The advantage of the melt-extrusion approach is lack of organic solvent and continuous production process. As the melt-extrusion is a novel pharmaceutical technique, the literature dealing with it is limited. The technical set-up involves a mixture and extrusion of itraconazole, hydroxypropyl-b-cyclodextrin (HP-b-CD), and hydroxypropylmethylcellulose (HPMC), in order to, by non-limiting example create a AUC shape-enhancing formulation of itraconazole. Cyclodextrin is a toroidal-shaped molecule with hydroxyl groups on the outer surface and a cavity in the center. Cyclodextrin sequesters the drug by forming an inclusion complex. The complex formation between cyclodextrins and drugs has been investigated extensively. It is known that water-soluble polymer interacts with cyclodextrin and drug in the course of complex formation to form a stabilized complex of drug and cyclodextrin co-complexed with the polymer. This complex is more stable than the classic cyclodextrin-drug complex. As one example, HPMC is water soluble; hence using this polymer with HP-b-CD in the melt is expected to create an aqueous soluble AUC shape-enhancing formulation. By non-limiting example, this approach may also be used to sequester and improve the water solubility of solid, AUC shape-enhancing formulations, for nanoparticle-based formulations.

Co-Precipitates

Co-precipitate itraconazole formulations may be prepared by formation of co-precipitates with pharmacologically inert, polymeric materials. It has been demonstrated that the formation of molecular solid dispersions or co-precipitates to create an AUC shape-enhancing formulations with various water-soluble polymers can significantly slow the in vitro dissolution rates and/or in vivo absorption. In preparing powdered products, grinding is generally used for reducing particle size, since the dissolution rate is strongly affected by particle size. Moreover, a strong force (such as grinding) may increase the surface energy and cause distortion of the crystal lattice as well as reducing particle size. Co-grinding itraconazole with hydroxypropylmethylcellulose, β-cyclodextrin, chitin and chitosan, crystalline cellulose, and gelatin, may enhance the dissolution properties such that AUC shape-enhancement is obtained. By non-limiting example, this approach may also be used to sequester and improve the water solubility of solid, AUC shape-enhancing formulations.

Dispersion-Enhancing Peptides

Compositions may include one or more di- or tripeptides containing two or more leucine residues. By further non-limiting example, U.S. Pat. No. 6,835,372 disclosing dispersion-enhancing peptides, is hereby incorporated by reference in its entirety. This patent describes the discovery that di-leucyl-containing dipeptides (e.g., dileucine) and tripeptides are superior in their ability to increase the dispersibility of powdered composition.

In another embodiment, highly dispersible particles including an amino acid are administered. Hydrophobic amino acids are preferred. Suitable amino acids include naturally occurring and non-naturally occurring hydrophobic amino acids. Some naturally occurring hydrophobic amino acids, including but not limited to, non-naturally occurring amino acids include, for example, beta-amino acids. Both D, L and racemic configurations of hydrophobic amino acids can be employed. Suitable hydrophobic amino acids can also include amino acid analogs. As used herein, an amino acid analog includes the D or L configuration of an amino acid having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. As used herein, aliphatic groups include straight chained, branched or cyclic C1-C8 hydrocarbons which are completely saturated, which contain one or two heteroatoms such as nitrogen, oxygen or sulfur and/or which contain one or more units of desaturation. Aromatic groups include carbocyclic aromatic groups such as phenyl and naphthyl and heterocyclic aromatic groups such as imidazolyl, indolyl, thienyl, furanyl, pyridyl, pyranyl, oxazolyl, benzothienyl, benzofuranyl, quinolinyl, isoquinolinyl and acridintyl.

Suitable substituents on an aliphatic, aromatic or benzyl group include —OH, halogen (—Br, —Cl, —I and —F)—O (aliphatic, substituted aliphatic, benzyl, substituted benzyl, aryl or substituted aryl group), —CN, —NO$_2$, —COOH, —NH$_2$, —NH (aliphatic group, substituted aliphatic, benzyl, substituted benzyl, aryl or substituted aryl group), —N(aliphatic group, substituted aliphatic, benzyl, substituted benzyl, aryl or substituted aryl group)$_2$, —COO (aliphatic group, substituted alipha tic, benzyl, substituted benzyl, aryl or substituted aryl group), —CONH$_2$, —CONH (aliphatic, substituted aliphatic group, benzyl, substituted benzyl, aryl or substituted aryl group)), —SH, —S(aliphatic, substituted aliphatic, benzyl, substituted benzyl, aromatic or substituted aromatic group) and —NH—C(.dbd.NH)—NH$_2$. A substituted benzylic or aromatic group can also have an aliphatic or substituted aliphatic group as a substituent. A substituted aliphatic group can also have a benzyl, substituted benzyl, aryl or substituted aryl group as a substituent. A substituted aliphatic, substituted aromatic or substituted benzyl group can have one or more substituents. Modifying an amino acid substituent can increase, for example, the lypophilicity or hydrophobicity of natural amino acids which are hydrophilic.

A number of the suitable amino acids, amino acids analogs and salts thereof can be obtained commercially. Others can be synthesized by methods known in the art.

Hydrophobicity is generally defined with respect to the partition of an amino acid between a nonpolar solvent and water. Hydrophobic amino acids are those acids which show a preference for the nonpolar solvent. Relative hydrophobicity of amino acids can be expressed on a hydrophobicity scale on which glycine has the value 0.5. On such a scale, amino acids which have a preference for water have values below 0.5 and those that have a preference for nonpolar solvents have a value above 0.5. As used herein, the term hydrophobic amino acid refers to an amino acid that, on the hydrophobicity scale, has a value greater or equal to 0.5, in other words, has a tendency to partition in the nonpolar acid which is at least equal to that of glycine.

Examples of amino acids which can be employed include, but are not limited to: glycine, proline, alanine, cysteine, methionine, valine, leucine, tyosine, isoleucine, phenylalanine, tryptophan. Preferred hydrophobic amino acids include leucine, isoleucine, alanine, valine, phenylalanine and glycine. Combinations of hydrophobic amino acids can also be employed. Furthermore, combinations of hydrophobic and hydrophilic (preferentially partitioning in water) amino acids, where the overall combination is hydrophobic, can also be employed.

The amino acid can be present in the particles of the invention in an amount of at least 10 weight %. Preferably, the amino acid can be present in the particles in an amount ranging from about 20 to about 80 weight %. The salt of a hydrophobic amino acid can be present in the particles of the invention in an amount of at least 10 weight percent. Preferably, the amino acid salt is present in the particles in an amount ranging from about 20 to about 80 weight %. In preferred embodiments the particles have a tap density of less than about 0.4 g/cm$^3$.

Methods of forming and delivering particles which include an amino acid are described in U.S. Pat. No. 6,586,008, entitled Use of Simple Amino Acids to Form Porous Particles During Spray Drying, the teachings of which are incorporated herein by reference in their entirety.

Proteins/Amino Acids

Protein excipients may include albumins such as human serum albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline. Dispersibility-enhancing peptide excipients include dimers, trimers, tetramers, and pentamers comprising one or more hydrophobic amino acid components such as those described above.

Carbohydrates

By non-limiting example, carbohydrate excipients may include monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol, isomalt, trehalose and the like.

Polymers

By non-limiting example, compositions may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (by non-limiting example cyclodextrins may include, 2-hydroxypropyl-beta-cyclodextrin, 2-hydroxypropyl-gamma-cyclodextrin, randomly methylated beta-cyclodextrin, dimethyl-alpha-cyclodextrin, dimethyl-beta-cyclodextrin, maltosyl-alpha-cyclodextrin, glucosyl-1-alpha-cyclodextrin, glucosyl-2-alpha-cyclodextrin, alpha-cyclodextrin, beta-cyclodextrin, gamma-cyclodextrin, and sulfobutylether-beta-cyclodextrin), polyethylene glycols, and pectin may also be used.

Highly dispersible particles administered comprise a bioactive agent and a biocompatible, and preferably biodegradable polymer, copolymer, or blend. The polymers may be tailored to optimize different characteristics of the particle including: i) interactions between the agent to be delivered and the polymer to provide stabilization of the agent and retention of activity upon delivery; ii) rate of polymer degradation and, thereby, rate of drug release profiles; iii) surface characteristics and targeting capabilities via chemical modification; and iv) particle porosity.

Surface eroding polymers such as polyanhydrides may be used to form the particles. For example, polyanhydrides such as poly[(p-carboxyphenoxy)hexane anhydride] (PCPH) may be used. Biodegradable polyanhydrides are described in U.S. Pat. No. 4,857,311. Bulk eroding polymers such as those based on polyesters including poly(hydroxy acids) also can be used. For example, polyglycolic acid (PGA), polylactic acid (PLA), or copolymers thereof may be used to form the particles. The polyester may also have a charged or functionalizable group, such as an amino acid. In a preferred embodiment, particles with controlled release properties can be formed of poly(D,L-lactic acid) and/or poly(DL-lactic-co-glycolic acid) ("PLGA") which incorporate a surfactant such as dipalmitoyl phosphatidylcholine (DPPC).

Other polymers include polyamides, polycarbonates, polyalkylenes such as polyethylene, polypropylene, poly (ethylene glycol), poly(ethylene oxide), poly(ethylene terephthalate), poly vinyl compounds such as polyvinyl alcohols, polyvinyl ethers, and polyvinyl esters, polymers of acrylic and methacrylic acids, celluloses and other polysaccharides, and peptides or proteins, or copolymers or blends thereof. Polymers may be selected with or modified to have the appropriate stability and degradation rates in vivo for different controlled drug delivery applications.

Highly dispersible particles can be formed from functionalized polyester graft copolymers, as described in Hrkach et al., (1995) Macromolecules, 28: 4736-4739; and Hrkach et al., "Poly(L-Lactic acid-co-amino acid) Graft Copolymers: A Class of Functional Biodegradable Biomaterials" in Hydrogels and Biodegradable Polymers for Bioapplications, ACS Symposium Series No. 627, Raphael M, Ottenbrite et al., Eds., American Chemical Society, Chapter 8, pp. 93-101, 1996.

In a preferred embodiment of the invention, highly dispersible particles including a bioactive agent and a phospholipid are administered. Examples of suitable phospholipids include, among others, phosphatidylcholines, phosphatidylethanolamines, phosphatidylglycerols, phosphatidylserines, phosphatidylinositols and combinations thereof. Specific examples of phospholipids include but are not limited to phosphatidylcholines dipalmitoyl phosphatidylcholine (DPPC), dipalmitoyl phosphatidylethanolamine (DPPE), distearoyl phosphatidycholine (DSPC), dipalmitoyl phosphatidyl glycerol (DPPG) or any combination thereof. Other phospholipids are known to those skilled in the art. In a preferred embodiment, the phospholipids are endogenous to the lung.

The phospholipid, can be present in the particles in an amount ranging from about 0 to about 90 weight %. More commonly, it can be present in the particles in an amount ranging from about 10 to about 60 weight %.

In another embodiment of the invention, the phospholipids or combinations thereof are selected to impart controlled release properties to the highly dispersible particles. The phase transition temperature of a specific phospholipid can be below, about or above the physiological body temperature of a patient. Preferred phase transition temperatures range from 30° C. to 50° C. (e.g., within +/−10 degrees of the normal body temperature of patient). By selecting phospholipids or combinations of phospholipids according to their phase transition temperature, the particles can be tailored to have controlled release properties. For example, by administering particles which include a phospholipid or combination of phospholipids which have a phase transition temperature higher than the patient's body temperature, the release of dopamine precursor, agonist or any combination of precursors and/or agonists can be slowed down. On the other hand, rapid release can be obtained by including in the particles phospholipids having lower transition temperatures.

Taste Masking, Flavor, Other

As also described above, itraconazole formulations disclosed herein and related compositions, may further include one or more taste-masking agents such as flavoring agents, inorganic salts (e.g., sodium chloride), sweeteners, antioxidants, antistatic agents, surfactants (e.g., polysorbates such as "TWEEN 20" and "TWEEN 80"), sorbitan esters, saccharin (e.g., sodium saccharin or other saccharin forms, which as noted elsewhere herein may be present in certain embodiments at specific concentrations or at specific molar ratios relative to itraconazole), bicarbonate, cyclodextrins, lipids (e.g., phospholipids such as lecithin and other phosphatidylcholines, phosphatidylethanolamines), fatty acids and fatty esters, steroids (e.g., cholesterol), and chelating agents (e.g., EDTA, zinc and other such suitable cations). Other pharmaceutical excipients and/or additives suitable for use in the compositions according to the invention are listed in "Remington: The Science & Practice of Pharmacy", 19th ed., Williams & Williams, (1995), and in the "Physician's Desk Reference", 52nd ed., Medical Economics, Montvale, N.J. (1998).

By way of non-limiting example, taste-masking agents in itraconazole formulations, may include the use of flavorings, sweeteners, and other various coating strategies, for instance, sugars such as sucrose, dextrose, and lactose, carboxylic acids, menthol, amino acids or amino acid derivatives such as arginine, lysine, and monosodium glutamate, and/or synthetic flavor oils and flavoring aromatics and/or natural oils, extracts from plants, leaves, flowers, fruits, etc. and combinations thereof. These may include cinnamon oils, oil of wintergreen, peppermint oils, clover oil, bay oil, anise oil, eucalyptus, vanilla, citrus oil such as lemon oil, orange oil, grape and grapefruit oil, fruit essences including apple, peach, pear, strawberry, raspberry, cherry, plum, pineapple, apricot, etc. Additional sweeteners include sucrose, dextrose, aspartame, acesulfame-K, sucralose and saccharin (e.g., sodium saccharin or other saccharin forms, which as noted elsewhere herein may be present in certain embodiments at specific concentrations or at specific molar ratios relative to itraconazole), organic acids (by non-limiting example citric acid and aspartic acid). Such flavors may be present at from about 0.05 to about 4 percent by weight, and may be present at lower or higher amounts as a factor of one or more of potency of the effect on flavor, solubility of the flavorant, effects of the flavorant on solubility or other physicochemical or pharmacokinetic properties of other formulation components, or other factors.

Another approach to improve or mask the unpleasant taste of an inhaled drug may be to decrease the drug's solubility, e.g., drugs must dissolve to interact with taste receptors. Hence, to deliver solid forms of the drug may avoid the taste response and result in the desired improved taste affect.

Moreover, taste-masking may be accomplished by creation of lipopilic vesicles. Additional coating or capping agents include dextrates (by non-limiting example cyclodextrins may include, 2-hydroxypropyl-beta-cyclodextrin, 2-hydroxypropyl-gamma-cyclodextrin, randomly methylated beta-cyclodextrin, dimethyl-alpha-cyclodextrin, dimethyl-beta-cyclodextrin, maltosyl-alpha-cyclodextrin, glucosyl-1-alpha-cyclodextrin, glucosyl-2-alpha-cyclodextrin, alpha-cyclodextrin, beta-cyclodextrin, gamma-cyclodextrin, and sulfobutylether-beta-cyclodextrin), modified celluloses such as ethyl cellulose, methyl cellulose, hydroxypropyl cellulose, hydroxylpropyl methyl cellulose, polyalkylene glycols, polyalkylene oxides, sugars and sugar alcohols, waxes, shellacs, acrylics and mixtures thereof.

An alternative according to certain other preferred embodiments is to include taste-modifying agents in the itraconazole formulation. These embodiments contemplate including in the formulation a taste-masking substance that is mixed with, coated onto or otherwise combined with itraconazole. Inclusion of one or more such agents in these formulations may also serve to improve the taste of additional pharmacologically active compounds that are included in the formulations in addition to itraconazole, e.g., another anti-fibrotic agent such as pirfenidone or pyridone analog compounds, or a mucolytic agent. Non-limiting examples of such taste-modifying substances include acid phospholipids, lysophospholipid, tocopherol polyethyleneglycol succinate, and embonic acid (pamoate). Many of these agents can be used alone or in combination with itraconazole or, in separate embodiments, itraconazole for aerosol administration.

Mucolytic Agents

Methods to produce formulations that combine agents to reduce sputum viscosity during aerosol treatment with itraconazole include the following. These agents can be prepared in fixed combination or be administered in succession with aerosol itraconazole therapy.

The most commonly prescribed agent is N-acetylcysteine (NAC), which depolymerizes mucus in vitro by breaking disulphide bridges between macromolecules. It is assumed that such reduction of sputum tenacity facilitates its removal from the respiratory tract. In addition, NAC may act as an oxygen radical scavenger. NAC can be taken either orally or by inhalation. Differences between these two methods of administration have not been formally studied. After oral administration, NAC is reduced to cysteine, a precursor of the antioxidant glutathione, in the liver and intestine. The antioxidant properties could be useful in preventing decline of lung function in cystic fibrosis (CF), chronic obstructive pulmonary disease (COPD) or pulmonary fibrotic diseases (e.g., idiopathic pulmonary fibrosis). Nebulized NAC is commonly prescribed to patients with CF, in particular in continental Europe, in order to improve expectoration of sputum by reducing its tenacity. The ultimate goal of this is to slow down the decline of lung function in CF.

L-lysine-N-acetylcysteinate (ACC) or Nacystelyn (NAL) is a novel mucoactive agent possessing mucolytic, antioxidant, and anti-inflammatory properties. Chemically, it is a salt of ACC. This drug appears to present an activity superior to its parent molecule ACC because of a synergistic mucolytic activity of L-lysine and ACC. Furthermore, its almost neutral pH (6.2) allows its administration in the lungs with a very low incidence of bronchospasm, which is not the case for the acidic ACC (pH 2.2). NAL is difficult to formulate in an inhaled form because the required lung dose is very high (approximately 2 mg) and the micronized drug is sticky and cohesive and it is thus problematic to produce a redispersable formulation. NAL was first developed as a chlorofluorocarbon (CFC) containing metered-dose inhaler (MDI) because this form was the easiest and the fastest to develop to begin the preclinical and the first clinical studies. NAL MDI delivered 2 mg per puff, from which approximately 10% was able to reach the lungs in healthy volunteers. One major inconvenience of this formulation was patient compliance because as many as 12 puffs were necessary to obtain the required dose. Furthermore, the progressive removal of CFC gases from medicinal products combined with the problems of coordination met in a large proportion of the patient population (12) have led to the development of a new galenical form of NAL. A dry powder inhaler (DPI) formulation was chosen to resolve the problems of compliance with MDIs and to combine it with an optimal, reproducible, and comfortable way to administer the drug to the widest possible patient population, including young children.

The DPI formulation of NAL involved the use of a nonconventional lactose (usually reserved for direct compression of tablets), namely, a roller-dried (RD) anhydrous beta-lactose. When tested in vitro with a monodose DPI device, this powder formulation produces a fine particle fraction (FPF) of at least 30% of the nominal dose, namely three times higher than that with MDIs. This approach may be used in combination with itraconazole for either co-administration or fixed combination therapy.

In addition to mucolytic activity, excessive neutrophil elastase activity within airways of cystic fibrosis (CF) patients results in progressive lung damage. Disruption of disulfide bonds on elastase by reducing agents may modify its enzymatic activity. Three naturally occurring dithiol reducing systems were examined for their effects on elastase activity: 1) *Escherichia coli* thioredoxin (Trx) system, 2) recombinant human thioredoxin (rhTrx) system, and 3) dihydrolipoic acid (DHLA). The Trx systems consisted of Trx, Trx reductase, and NADPH. As shown by spectrophotometric assay of elastase activity, the two Trx systems and DHLA inhibited purified human neutrophil elastase as well as the elastolytic activity present in the soluble phase (sol) of CF sputum. Removal of any of the three Trx system constituents prevented inhibition. Compared with the monothiols N-acetylcysteine and reduced glutathione, the dithiols displayed greater elastase inhibition. To streamline Trx as an investigational tool, a stable reduced form of rhTrx was synthesized and used as a single component. Reduced rhTrx inhibited purified elastase and CF sputum sol elastase without NADPH or Trx reductase. Because Trx and DHLA have mucolytic effects, we investigated changes in elastase activity after mucolytic treatment. Unprocessed CF sputum was directly treated with reduced rhTrx, the Trx system, DHLA, or DNase. The Trx system and DHLA did not increase elastase activity, whereas reduced rhTrx treatment increased sol elastase activity by 60%. By contrast, the elastase activity after DNase treatment increased by 190%. The ability of Trx and DHLA to limit elastase activity combined with their mucolytic effects makes these compounds potential therapies for CF.

In addition, bundles of F-actin and DNA present in the sputum of cystic fibrosis (CF) patients but absent from normal airway fluid contribute to the altered viscoelastic properties of sputum that inhibit clearance of infected airway fluid and exacerbate the pathology of CF. One approach to alter these adverse properties is to remove these filamentous aggregates using DNase to enzymatically depolymerize DNA to constituent monomers and gelsolin to sever F-actin to small fragments. The high densities of negative surface charge on DNA and F-actin suggest that the bundles of these filaments, which alone exhibit a strong electrostatic repulsion, may be stabilized by multivalent cations such as histones, antimicrobial peptides, and other positively charged molecules prevalent in airway fluid. Furthermore, as a matter-a-fact, it has been observed that bundles of DNA or F-actin formed after addition of histone H1 or lysozyme are efficiently dissolved by soluble multivalent anions such as polymeric aspartate or glutamate. Addition of poly-aspartate or poly-glutamate also disperses DNA and actin-containing bundles in CF sputum and lowers the elastic moduli of these samples to levels comparable to those obtained after treatment with DNase I or gelsolin. Addition of poly-aspartic acid also increased DNase activity when added to samples containing DNA bundles formed with histone H1. When added to CF sputum, poly-aspartic acid significantly reduced the growth of bacteria, suggesting activation of endogenous antibacterial factors. These findings suggest that soluble multivalent anions have potential alone or in combination with other mucolytic agents to selectively dissociate the large bundles of charged biopolymers that form in CF sputum.

Hence, NAC, unfractionated heparin, reduced glutathione, dithiols, Trx, DHLA, other monothiols, DNAse, dornase alfa, hypertonic formulations (e.g., osmolalities greater than about 350 mOsmol/kg), multivalent anions such as polymeric aspartate or glutamate, glycosidases and other examples listed above can be combined with itraconazole and other mucolytic agents for aerosol administration to improve anti-fibrotic and/or anti-inflammatory activity through better distribution from reduced sputum viscosity, and improved clinical outcome through improved pulmonary function (from improved sputum mobility and muco-ciliary clearance) and decreased lung tissue damage from the immune inflammatory response.

In some embodiments, the method further comprises administration of one or more additional therapeutic agents to the mammal.

EXAMPLES

Because the relevancy to human efficacy in bleomycin-induced lung fibrosis mouse model, though well established in preclinical studies (Moeller, 2008), has not been established, a new version of the bleomycin-induced lung fibrosis mouse study protocol was designed, with marketed anti-fibrotic drugs, namely pirfenidone and nintedanib, as positive controls. Another anti-fungal agent, Fluconazole, was also tested to show that anti-fungal activities alone cannot reduce lung fibrosis.

Our study showed that treatment of itraconazole alone at 7.5 and 15 mg/kg, which led to plasma exposure levels at 394±66 and 899±192 ng/mL, resulted in significant reduction in fibrotic activity, including reduction in 1) modified Ashcroft score, 2) stained area for collagen, inflammation and αSMA.

Typical dose levels of itraconazole in the clinic are 100 mg (PO/QD), 200 mg (PO/QD) or 200 mg (PO/BID). Peak plasma levels are reached 2-5 hours post oral dose. As a consequence of non-linear pharmacokinetics, itraconazole accumulates in plasma during multiple dosing. Steady state plasma levels are generally reached around 15 days post oral administration. Cmax at steady state were reported at 500 ng/mL at 100 mg (PO/QD), 1100 ng/mL at 200 mg (PO/QD) and 2000 ng/mL at 200 mg (PO/BID), respectively (Sporanox-itraconazole capsule product label), indicating that efficacious dose levels observed at 7.5 mg/kg and 15 mg/kg in our model study are well within the clinically acceptable doses.

Furthermore, in the same study, it was found that the anti-fibrotic activity of itraconazole is better than that of pirfenidone at 200 mg/kg, and comparable if not better than that of nintedanib at 60 mg/kg, an agent recently approved for treating patients with IPF.

Also, the studies have demonstrated that Fluconazole, another anti-fungal agent with structural similarity to itraconazole, did not show detectable changes in fibrosis related endpoint measurements at 70 mg/kg daily dose which resulted in plasma level of 56090±4947 ng/mL, over 62-fold higher than that of itraconazole at 15 mg/kg.

While an exact mechanism for its anti-fibrotic activity is not clear at the moment, it is believed that treatment of itraconazole will be beneficial to patients of IPF, and propose to treat IPF patients with itraconazole either alone or in combination of other agents that may possess beneficial effects to IPF patients. Itraconazole may be administered intravenously, intranasal/intratracheally or orally.

Oral dosing of itraconazole were compared to those from various inhalation formulations of itraconazole in the bleomycin-induced mouse model, and improved efficacy of itraconazole treatment in mouse model can be achieved, which greatly lower the efficacious dose for lung-fibrosis treatment to reduce possible side effects, especially in long-term uses.

Example 1 Establishment of Positive and Negative Controls

Forty male C57BL/6 mice (Nanjing Biomedical Research Institute of Nanjing University) were randomly divided into two groups on Day 1, 10 animals for one group (referred to as Control group or Group 1) and 30 for the other. The animals in the Control group were administered intratracheally with PBS at a dose of 2 mL/kg while the others were administered intratracheally with bleomycin (Cat #HY-17565, MCE) at a dose of 0.66 mg/kg.

On Day 5, the mice with bleomycin treatment were divided into three groups at random (referred to as Group 2-4, n=10), and orally administered with vehicle (0.5% Methyl cellulose), nintedanib (Kangmanlin Co. Ltd., prepared in 0.5% Methyl cellulose with a final concentration of 6.0 mg/mL) and fluconazole (Kangmanlin Co. Ltd., prepared in 0.5% Methyl cellulose with a final concentration of 7.0 mg/mL) at daily doses of 10 mL/kg, 60 mg/kg and 70 mg/kg, respectively. The mice in the Control group was administered with vehicle (0.5% Methyl cellulose) at a daily dose of 10 mL/kg. Mice body weights were measured and recorded on Day 1, 5, 12, 19 and 25.

Two hours post drug administration on Day 25, all animals were anaesthetized with pentobarbital (i.p., 65 mg/kg). Blood samples were collected from orbital vein, put in tubes pre-coated with EDTA-K2 (KANG JIAN, Cat #KJ202), centrifuged at 4000×g for 10 minutes at 4° C. and then stored at −80° C. for determination of plasma drug levels. Then, the trachea was exposed, and bronchoalveolar lavage fluid (BALF) was collected from each mouse by injecting 0.3 mL of saline into trachea close to the larynx for three times. After BALF collection, mice were perfused with saline, and all four lung lobes were collected from each mouse, fixed in 10% NBF solution, embedded in paraffin and cut into 5 μm-thick sections. The sections were de-paraffinized with xylene and ethanol and subject to Haematoxylin-Eosin, Masson Trichrome and α-SMA IHC staining.

The bronchoalveolar lavage fluid of 20 μL was mixed with 20 μL of trypan blue to determine the cell number. Then, the cells in the BALF were concentrated using a Cytospinat at 1,000 rpm for 5 minutes, smeared on slides and then stained with Diff-Quik stain. Cell types (alveolar macrophages, neutrophils, or lymphocytes) were determined by counting at least 200 cells using a standard hemocytometer. The rest BALFs were centrifuged and supernatants were collected and stored at −80° C. for soluble collagen analysis.

The Haematoxylin-Eosin staining was used to identify and quantitate the inflammatory cells in the tissues, and the total inflammation area was calculated using the AperioScanScope software.

The sections with Masson Trichrome staining were scored for pulmonary fibrosis according to the modified Ashcroft fibrosis rating criteria in Table 1 below. Each lung lobe was divided into 4 parts according to the distance from the main bronchus, i.e., the upper, upper middle, lower middle and lower parts, which were scored separately and averaged later.

TABLE 1

| Modified Ashcroft Score | |
| --- | --- |
| Grade of Fibrosis | Characterization of the Modified Ashcroft Score |
| 0 | Alveolar septa: No fibrotic burden at the most flimsy small fibers in some alveolar walls Lung structure: Normal lung |
| 1 | Alveolar septa: Isolated gentle fibrotic changes (septum ≤3x thicker than normal) Lung structure: Alveoli partly enlarged and rarefied, but no fibrotic masses present |
| 2 | Alveolar septa: Clearly fibrotic changes (septum >3x thicker than normal) with knot-like formation but not connected to each other Lung structure: Alveoli partly enlarged and rarefied, but no fibrotic masses |
| 3 | Alveolar septa: Contiguous fibrotic walls (septum >3x thicker than normal) predominantly in whole microscopic field Lung structure: Alveoli partly enlarged and rarefied, but no fibrotic masses |
| 4 | Alveolar septa: Variable Lung structure: Single fibrotic masses (≤10% of microscopic field) |
| 5 | Alveolvar septa: Variable Lung structure: Confluent fibrotic masses (>10 and ≤50% of microscopic field). Lung structure severely damaged but still preserved |

TABLE 1-continued

Modified Ashcroft Score

Grade of
Fibrosis Characterization of the Modified Ashcroft Score

| | |
|---|---|
| 6 | Alveolar septa: Variable, mostly not existent<br>Lung structure: Large contiguous fibrotic masses (>50% of microscopic field).<br>Lung architecture mostly not preserved |
| 7 | Alveolar septa: non-existent<br>Lung structure: Alveoli nearly obliterated with fibrous<br>masses but still up to five air bubbles |
| 8 | Alveolar septa: non-existent<br>Lung structure: Microscopic field with complete obliteration with fibrotic masses |

α-SMA is a well characterized marker in fibrosis. Immunohistochemistry staining of α-SMA is often used to characterize and quantitate the tissue fibrosis. Increased staining of α-SMA often reflects accumulation of collagen-producing myofibroblasts. Before α-SMA IHC staining, the deparaffinized sections were treated with citrate antigen retrieval solution (0.01 N citrate buffer, pH 6.0) at 100° C. for 10 minutes, and then incubated with rabbit polyclonal anti-α-SMA (1:400, ab5694, Abcam) for 1 hour followed by goat anti-rabbit HRP (K4003, Dako). DAB substrate kit (DAB0031, Maixin, Shanghai) was used for chromogenic staining. All sections were further counter-stained with hematoxylin. Red α-SMA staining areas were calculated using the AperioImageScope program.

Statistical analysis was performed using student's T-test, one-way or two-way ANOVA followed by post-hoc Dunnett's test if significant. Non-parametric test like Mann-Whitney was used when N was too small or data did not follow Gaussian distribution. The difference was considered significant when $p<0.05$. *$p<0.05$, $p<0.01$, *$p<0.01$.

Mice body weight changes were shown in FIG. 1. Mice in Group 1 had their body weights increased as the experiment proceeded while the body weights of mice in other groups decreased slightly or remain unchanged. The two-hour post dosing plasma levels were 1079 ng/mL and 56090 ng/mL for nintedanib and fluconazole, respectively.

Figure 2:
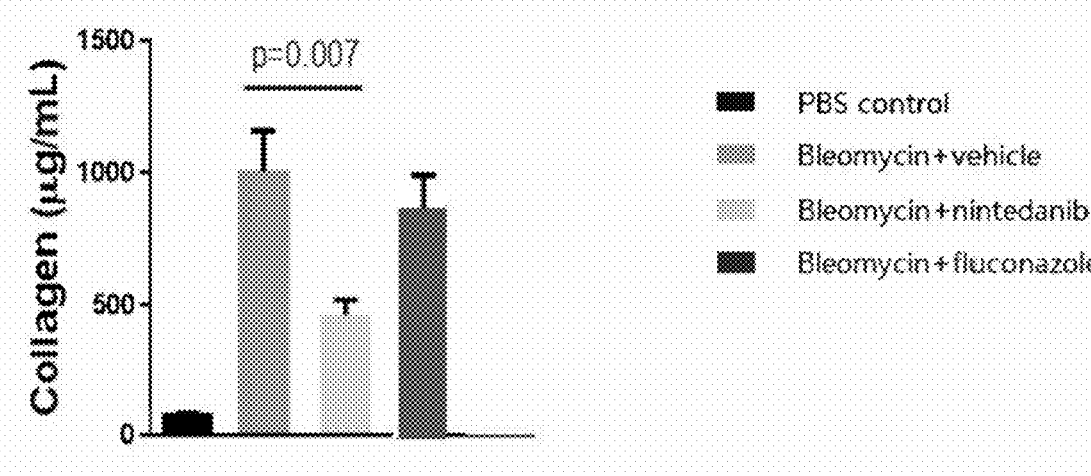
FIG. 2 shows BALF collagen levels following bleomycin plus nintedanib or fluconazole treatment.
Figure 3:
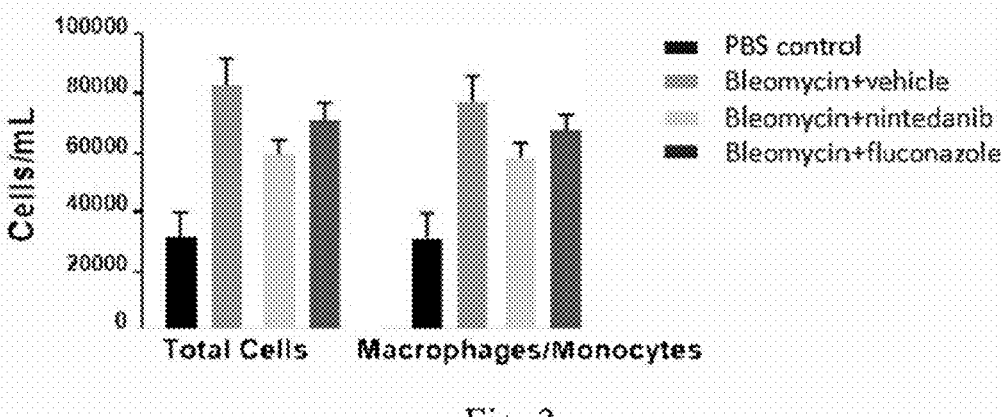
FIG. 3 shows total cell number (left four columns) and macrophage number (right four columns) in BALFs following bleomycin plus nintedanib or fluconazole treatment.

Bleomycin caused increase in BALF collagen levels, indicating elevated inflammatory and fibrotic responses, as shown in FIG. 2, but treatment with nintedanib significantly reduced collagen levels. No collagen level reduction was observed in animals administered with fluconazole. Bleomycin treatment also increased total cell number and macrophage/monocyte number, and treatment with nintedanib reduced cell number to some extent, see FIG. 3.

Figures 4, 5:
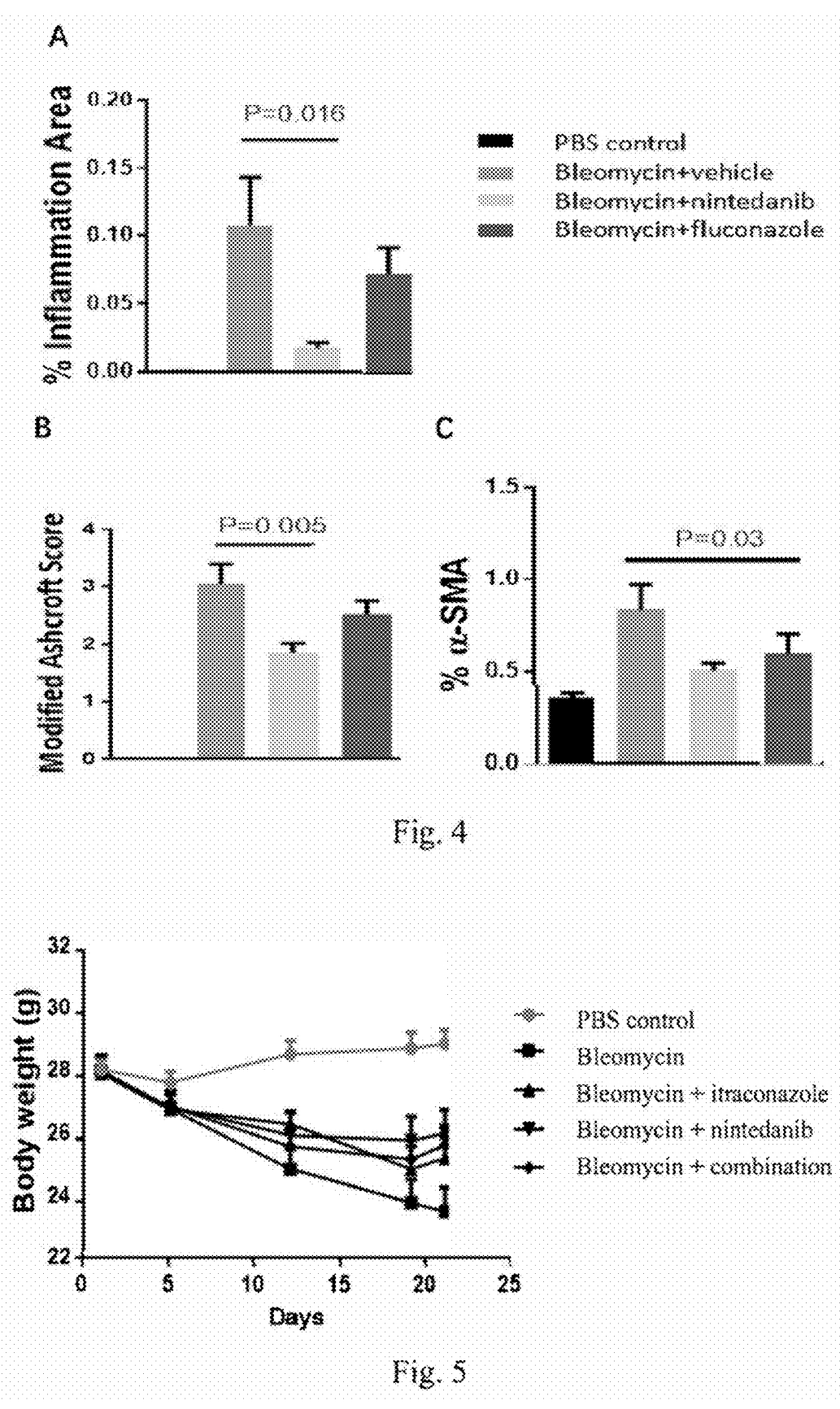
FIG. 4 shows inflammation area (panel A), modified Ashcroft score (panel B) and α-SMA staining (panel C) of mice lungs following bleomycin plus nintedanib or fluconazole treatment.
FIG. 5 shows mice body weight changes following bleomycin treatment plus itraconazole, nintedanib or combination administration.

FIG. 4 (panel A-C) showed the Haematoxylin-Eosin, Masson Trichrome and α-SMA IHC staining analysis results. As expected, administration of bleomycin resulted in more inflammation areas, higher modified Ashcroft score and increased α-SMA staining in lungs. Nintedanib administration significantly reduced lung inflammation area, modified Ashcroft score and α-SMA staining area (by 84%, 39% and 39%, respectively), which was not observed following fluconazole treatment.

It is of critical importance that the results of our anti-IPF efficacy studies are reproducible and can be compared to those from different studies of different drugs in the same animal disease model. By using nintedanib (a marketed IPF drug) as the positive control and fluconazole (a marketed azole class antifungal drug) as the negative control in Bleomycin induced IPF mouse model, the validity of the animal model was confirmed, and the study above using the animal model recapitulated the known anti-IPF efficacies of nintedanib.

In addition, although measured plasma levels passed the antifungal efficacious levels, fluconazole failed to show any significant anti-IPF activities, whereas nintedanib was efficacious. The results from this study clearly demonstrated that antifungal activities known for this class of drugs cannot be translated directly to anti-IPF activities.

Example 2 Oral and Combination Treatment of Itraconazole Inhibited Fibrosis

Fifty male C57BL/6 mice (Gempharmatech Co., Ltd.) were randomly divided into two groups on Day 1, 10 animals for one group (referred to as Control group or Group 1) and 40 for the other. The animals in the Control group were administered intratracheally with PBS at a dose of 2 mL/kg while the others were administered intratracheally with bleomycin (Cat #HY-17565, MCE) at a dose of 0.66 mg/kg.

On Day 5, the mice with bleomycin treatment were divided into four groups at random (referred to as Group 2-5, n=10), and orally administered with vehicle (DMSO: PEG400=1:9, V/V), itraconazole (Kangmanlin Co. Ltd. prepared in DMSO/PEG400 with a final concentration of 1.5 mg/mL), nintedanib (Kangmanlin Co. Ltd., prepared in DMSO/PEG400 with a final concentration of 6.0 mg/mL), and itraconazole+nintedanib (prepared in DMSO/PEG400 with final concentrations of 1.5 mg/mL and 6.0 mg/mL) at daily doses of 10 mL/kg, 15 mg/kg, 60 mg/kg and 15+60 mg/kg, respectively. The mice in the Control group was administered with vehicle (DMSO/PEG400) at a daily dose of 10 mL/kg. Mice body weights were measured and recorded on Day 1, 5, 12, 19 and 21.

Two hours post drug administration on Day 21, all animals were anaesthetized with pentobarbital (i.p., 60 mg/kg). Blood sample, bronchoalveolar lavage fluid (BALF) and lung lobes were collected from each mouse and then processed following the protocols in Example 1.

The two-hour post dosing plasma levels were 700 ng/mL and 310 ng/mL for itraconazole and nintedanib, respectively. When itraconazole and nintedanib were combined in administration, the plasma drug levels were 518 ng/mL and 397 ng/mL, respectively.

Mice body weights during the experiment were recorded and shown in FIG. 5. It can be seen that itraconazole and/or nintedanib administration inhibited bleomycin-induced body weight reduction to some extent.

Figures 6, 7:
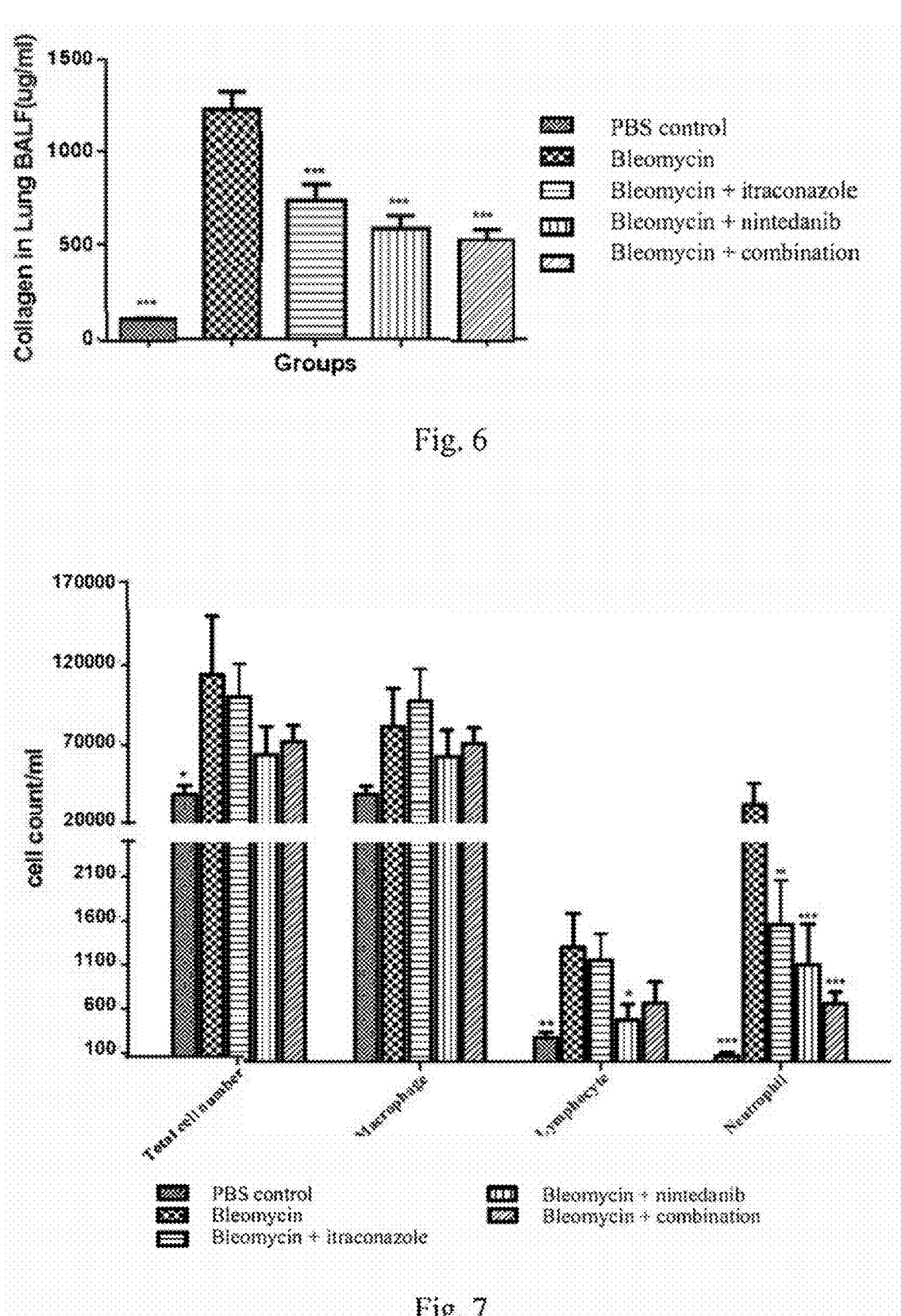
FIG. 6 shows BALF collagen levels following bleomycin treatment plus itraconazole, nintedanib or combination administration.
FIG. 7 shows cell counts in BALFs following bleomycin treatment plus itraconazole, nintedanib or combination administration.
Figures 8, 9:
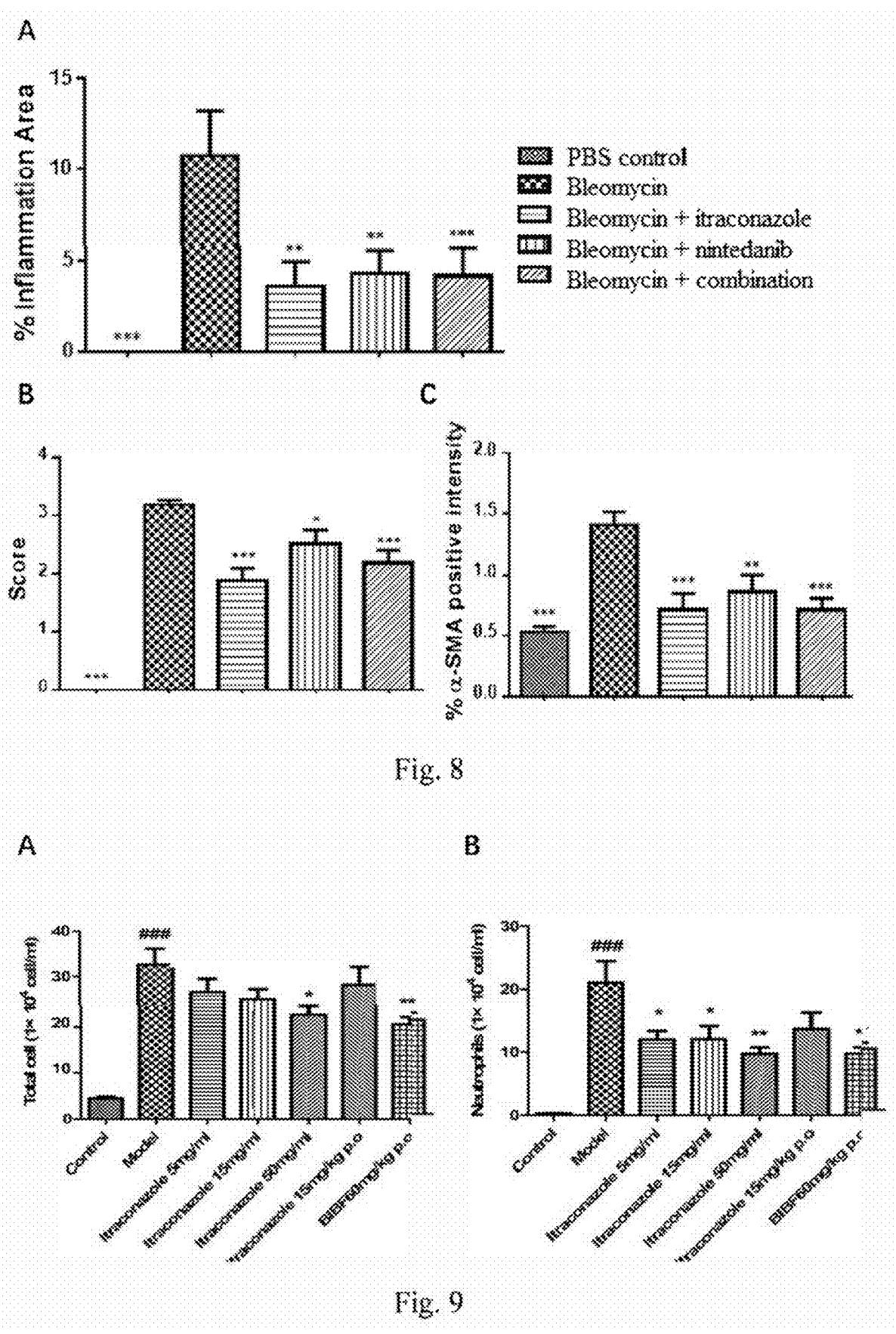
FIG. 8 shows inflammation area (panel A), modified Ashcroft score (panel B) and a-SMA staining (panel C) of mice lungs following bleomycin treatment plus itraconazole, nintedanib or combination administration.
FIG. 9 shows total cell number (panel A) and neutrophil number (panel B) in BALFs following bleomycin treatment plus inhalation or oral administration of itraconazole, or nintedanib.

BALF collagen and cytological analysis results were shown in FIG. 6-7. Compared to the model group, i.e., Group 2, the collagen level and neutrophil number were reduced in animals following itraconazole, nintedanib and combination administration. In addition, itraconazole, nintedanib and combination administration significantly reduced lung inflammation area, modified Ashcroft score and α-SMA staining area as compared to the model group caused by bleomycin treatment, as shown in FIG. 8 (panel A-C).

Studies on itraconazole and its combination with nintedanib in bleomycin induced IPF mouse model clearly demonstrated that itraconazole was highly efficacious against IPF at its clinically acceptable plasma levels, and was comparable favorably to marketed anti-IPF drug nintenanib. All indicators, from collagen content in BALF to inflammatory cell counts, to histopathological images, showed significant improvement by the end of the study. Based on the negative results of fluconazole from the study in Example 1, the activities observed for itraconazole was unlikely from its known antifungal activities, and a new mode of action must be involved. Further, signs of improvement were observed in the combination therapy as compared to respective mono-therapies (see FIGS. 6-7), and further studies were needed.

Example 3 Inhalation Treatment of Itraconazole Inhibited Fibrosis

Sixty male ICR mice (SHANGHAI SLAC LABORATORY ANIMAL CO., LTD) were randomly divided into two groups on Day 1, 10 animals for one group (referred to as Control group or Group 1) and 50 for the other. The mice were anesthetized by intraperitoneal injection of 1.5% pentobarbital sodium solution at a dose of 0.1 mL/20 g, and then supinely positioned and immobilized. Iodine was used to disinfect the neck hair and skin. Later, the neck skin was cut to expose the trachea. 50 μL of PBS or bleomycin hydrochloride (Hisun Pfizer pharmaceutical Co., LTD, 17001711) in 0.9% sodium chloride solution (0.35 USP/ml, i.e., 350 bleomycin units/mL) was quickly sprayed as mist into the trachea of mice from the Control Group or the other group with a high pressure syringe connected to a spraying nozzle. At the end, the skin was sutured and disinfected, and the mice were returned to the cages for recovery.

On Day 5, the mice treated with bleomycin were divided into six groups at random (referred to as Group 2-7). Drug administration was performed from Day 5-27 according to the dosing scheme in Table 2 below.

For itraconazole inhalation, each mouse was placed in a 16×13×9 (length×width×height in cm) cabinet. Itraconazole preparation of 5, 15 or 50 mg/mL was sprayed into the cabinet with a compressed nebulizer.

After 50 mg/mL itraconazole preparation was fully filled in the cabinet, a 50 mL syringe (containing 2 mL of mobile phase for liquid chromatography) was used to suck 48 mL of atomized liquid for determination of itraconazole's concentration. The syringe was sealed, stayed still for 10 minutes, sharply shaken and then sent for liquid chromatography (LC). The mobile phase for LC was Acetonitrile-phosphate buffer (65:35) (6.8 g $KH_2PO_4$ dissolved in 1000 mL pure water, then pH value adjusted to 7.0 with NaOH), and the flow rate was 1.0 mL/min. The Kromasil C18 (4.6×150 mm, 5 μm) was used as the chromatographic column with a column temperature of 30° C. Detection wavelength was set at 256 nm, and the sample volume for injection was 50 μL.

TABLE 2

| | | Animal grouping and dosing scheme | | |
|---|---|---|---|---|
| Group no. | Animal number | Drug | Dose | Treatment |
| 1 | 10 | ethanol | 3 min/day | inhale, q.d. |
| 2 | 8 | ethanol | 3 min/day | inhale, q.d. |
| 3 | 8 | itraconazole hydrochloride (FrontHealth) in ethanol, 5 mg/mL | 3 min/day | inhale, q.d. |
| 4 | 8 | itraconazole hydrochloride in ethanol, 15 mg/mL | 3 min/day | inhale, q.d. |
| 5 | 9 | itraconazole hydrochloride in ethanol, 50 mg/mL | 3 min/day | inhale, q.d. |
| 6 | 8 | itraconazole hydrochloride in 0.5% sodium carboxymethyl cellulose, 1.5 mg/mL | 15 mg/kg body weight | p.o., q.d. |
| 7 | 8 | nintedanib (BIBF, Kangmanlin Co., Ltd) in 0.9% sodium chloride, 6 mg/mL | 60 mg/kg body weight | p.o., q.d. |

Twenty-four hours after the last drug administration, the mice were sacrificed by dislocation of cervical vertebra. The trachea was isolated and intubated. The upper lobe of the left lung was ligated. Alveolar lavage was performed with 0.5 mL of alveolar lavage solution for 3 times, which was later mixed together and referred to as BALF. The total number of leukocytes in the BALF was counted. The BALF was centrifuged at 2000 rpm/min for 10 min at 4° C. The supernatant was collected and stored at −80° C. for cytokine measurement, and the deposit was smeared on glass slides. After air drying at room temperature, the slides were subjected to Wright's-Giemsa staining. The number of neutrophils, lymphocytes and macrophages were counted under a microscope from a total of 200 cells for each slide. The upper left lung tissues were used for measuring the level of hydroxyproline, and the lower part was fixed in formalin for H&E staining and Masson's staining.

The level of hydroxyproline in the lung tissues was measured using a Hydroxyproline Assay kit (Nanjing JianCheng Bioengineering Institute). The level of TGF-β1 in 100 μL BALF was determined using a mouse TGF-β1 ELISA kit (Beijing 4A Biotech Co., LTD), and the level of type I collagen (Col I) in 100 μL BALF was determined using a mouse Collagen Type I ELISA kit (CUSABIO BIOTEH).

The lower part lung tissues were washed overnight in running water, then gradually dehydrated in 70%-100% ethanol, immersed in xylene and embedded in paraffin. Then, the lung tissues were sectioned into 4 μm-thick sections for H&E staining and Masson's staining. H&E staining was used to observe the alveolar hyperemia, the infiltration or aggregation of neutrophils in the alveolar space or the vascular wall, and the thickening of alveolar septum or the formation of hyaline membranes. The degree of fibrosis in the lesions with H&E staining was observed under microscope and scored using a semi-quantitative Ashcroft scoring criteria below. Grade 0: Normal tracheal bronchoalveolar structures; Grade 1: Minimal fibrous thickening of alveolar or bronchiolar walls; Grade 3: Moderate thickening of walls without obvious damage to lung architecture; Grade 5: Increased fibrosis with definite damage to lung structure and formation of fibrous bands or small fibrous masses; Grade 7: Severe distortion of structure and large fibrous areas, with honeycomb lung placed in this category; Grade 8: Total fibrous obliteration. The severity of fibrosis between two odd numbers was considered as the corresponding even number. On the other hand, IOD value of positive Masson's staining site was measured by Image pro software for analysis.

The data were tested for the homogeneity of variance. If the variance was homogenous (p>0.05), a single factor variance analysis was performed. The Dunnet test was performed for the differences between each dose group and the control group. If the variance was heterogenous (p 0.05), a non-parametric test was conducted, followed by the mann-whitney U test for examining the differences between each dose group and the control group. The difference was considered significant when p<0.05.

Determination of itraconazole concentration by high performance liquid chromatography obtained a standard curve Y=93079X-9553.5, $r^2 \geq 0.999$, where X represented itraconazole concentration and Y represented peak area, with a faithful linear relationship within the range of 0.1 to 114.5 µg/mL. The mean concentration of itraconazole in the mobile phase was determined to be 69.08 µg/mL, so the itraconazole concentration in the cabinet was 2.88 µg/mL. Given that mouse's minute ventilation volume was about 24 mL/min, the daily doses for itraconazole inhalation at 50, 15 and 5 mg/mL were calculated to be about 8.3, 2.5 and 0.8 mg/kg, respectively.

The number of total leukocytes, neutrophils, lymphocytes and macrophages in the BALF increased significantly (p<0.001) on Day 28 due to bleomycin treatment. Itraconazole inhalation treatment at 5, 15 and 50 mg/mL for 3 min/day for 22 days reduced the total number of leukocytes in the BALF in a dose dependent manner. Compared with the model group (Group 2), itraconazole inhalation at 50 mg/ml significantly inhibited the increase of the total number of leukocytes (p<0.05). Itraconazole inhalation at 5, 15, 50 mg/mL for 3 min significantly inhibited the increases in neutrophils in the BALF (p<0.05~0.01), but had no effects on the number of lymphocytes and macrophages. Oral administration of nintedanib at 60 mg/kg as a positive control significantly reduced the total number of leukocytes and neutrophils in the BALF (p<0.01), but had no effects on the number of lymphocytes and macrophages. The results were shown in FIG. 9 (panel A and B).

Due to bleomycin treatment, the level of TGF-β1 significantly increased in the BALF on Day 28 (p<0.001). Itraconazole inhalation at 5, 15, 50 mg/mL for 3 min/day for 22 days dose-dependently decreased the level of TGF-β1 in the BALF. Compared with the model group, the itraconazole inhalation at 5 mg/mL and 50 mg/mL significantly reduced the level of TGF-β1 content in the BALF (p<0.05~0.001). The level of TGF-β1 in the BALF following itraconazole inhalation at 15 mg/mL had a trend of decrease but with a large standard deviation. The level of TGF-β1 in the BALF was also significantly reduced by oral administration of nintedanib at 60 mg/kg (p<0.001, FIG. 10, panel A).

Figures 10, 11:
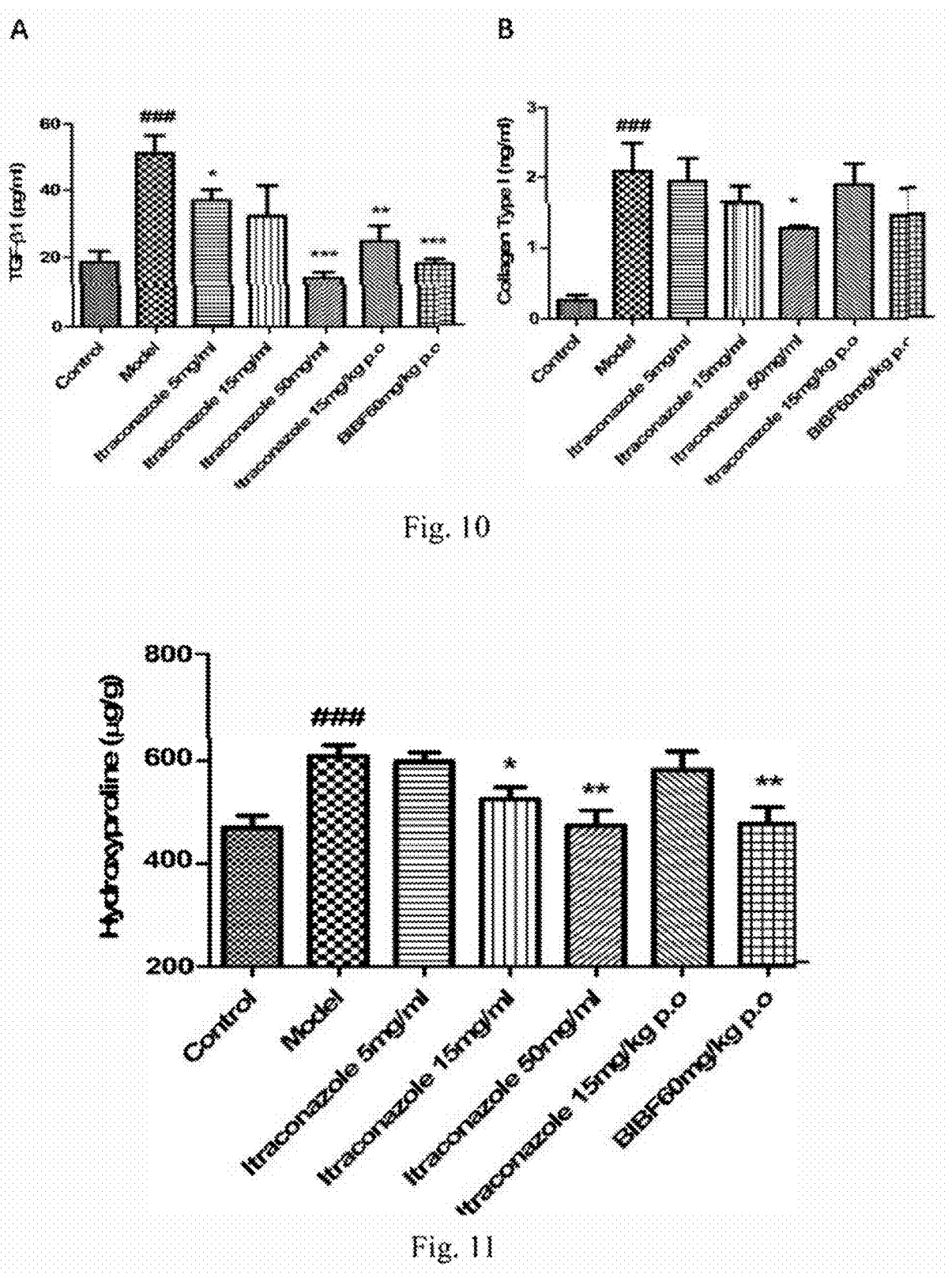
FIG. 10 shows TGF-β1 levels (panel A) and collagen type I levels (panel B) in BALFs following bleomycin treatment plus inhalation or oral administration of itraconazole, or nintedanib.
FIG. 11 shows hydroxyproline levels in lungs following bleomycin treatment plus inhalation or oral administration of itraconazole, or nintedanib.

With bleomycin treatment, the level of Col I in the BALF increased significantly on Day 28 (p<0.001). Itraconazole inhalation at 5, 15, 50 mg/mL for 3 min for 22 days dose-dependently reduced the level of Col I in the BALF. Compared with the model group, itraconazole inhalation at 50 mg/mL significantly reduced the level of Col I in the BALF (p<0.05). Oral administration of nintedanib 60 mg/kg did not reduce the level of Col I in the BALF (FIG. 10, panel B).

The level of hydroxyproline in the lung tissues increased significantly on Day 28 (p<0.001). Itraconazole inhalation at 5, 15 and 50 mg/mL for 3 min/day for 22 days dose-dependently suppressed the level of hydroxyproline in the lung tissues. Compared with the model group, the level of hydroxyproline in the lung tissues were decreased significantly in the 15 and 50 mg/mL administration groups (p<0.05~0.01). Oral administration of nintedanib at 60 mg/kg significantly reduced the level of hydroxyproline in the lung tissues (p<0.01). The results were shown in FIG. 11.

Figures 12, 13:
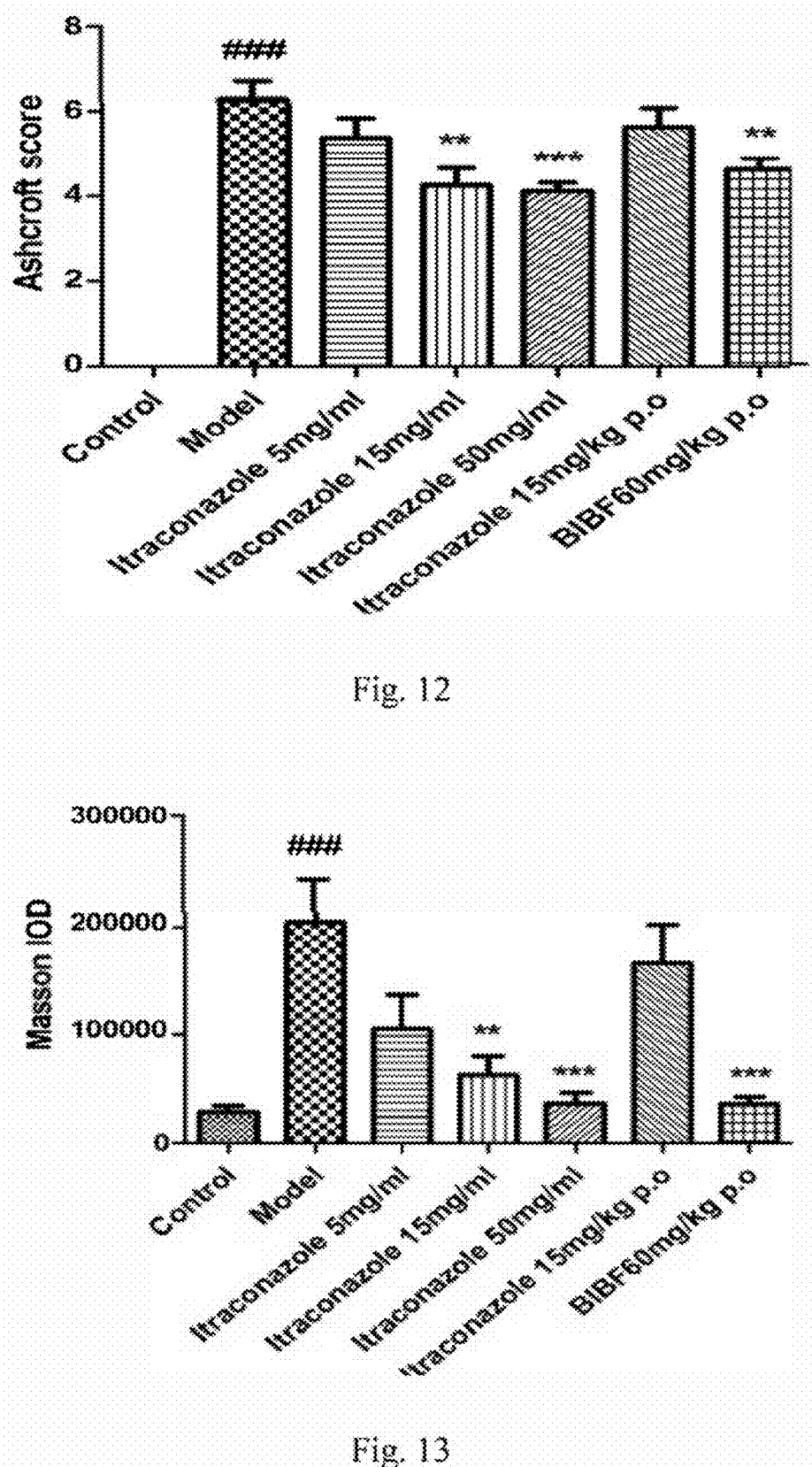
FIG. 12 shows Ashcroft scores of mice lung tissues following bleomycin treatment plus inhalation or oral administration of itraconazole, or nintedanib.
FIG. 13 shows Masson IODs in the lung tissues following bleomycin treatment plus inhalation or oral administration of itraconazole, or nintedanib.

On Day 28, lung tissues were performed for H&E staining followed by a microscopic observation, where an obvious alveolar hyperemia was observed. A large number of neutrophils and macrophages infiltrated around the small airway. Alveolar septum were thickened, hyaline membrane was formed, and lung tissues were compacted. Itraconazole inhalation at 15, 50 mg/mL significantly alleviated the pathological changes observed in the mouse model of pulmonary fibrosis, but the inhalation dose of 5 mg/mL did not alleviate the pathological changes. Oral administration of nintedanib at 60 mg/kg significantly reduced the infiltration of neutrophils and macrophages and the thickening of alveolar septum in the lung tissues. Semi-quantitative Ashcroft Score showed that itraconazole inhalation at 5, 15, 50 mg/mL dose-dependently reduced the pulmonary fibrosis in mice, and oral administration of nintedanib at 60 mg/kg significantly reduced the pulmonary fibrosis too (p<0.01, FIG. 12).

On Day 28, Masson's staining was done followed by a microscopic observation and semi-quantitative analysis using image pro software. Collagen deposition in the lungs was observed in the model group while itraconazole inhalation at 5, 15, 50 mg/mL dose-dependently reduced the collagen deposition. Compared with the model group, itraconazole inhalation at 15 or 50 mg/mL significantly reduced the collagen deposition in the lung tissues (p<0.01~0.001), and oral administration of nintedanib at 60 mg/kg also significantly reduced the collagen deposition (p<0.001, FIG. 13).

In a separate experiment, three groups of healthy male mice were treated with itraconazole for 5 consecutive days. Animals in Group A were orally administered with itraconazole in DMSO:PEG400 (1:9, v/v) at a daily dose of 15 mg/kg, while mice in Group B and C were subject to 3-min inhalation treatment of itraconazole of 15 mg/mL and 50 mg/mL, respectively. Two hours after the last dose, plasma samples and lung tissues were collected as described above. These samples were sent to an independent bioanalytical service lab to determine the levels of itraconazole, and results were summarized in Table 3.

TABLE 3

| Average drug concentrations in plasma and lung tissues | | | |
|---|---|---|---|
| Group no. | Drug Administration | Plasma Concentrations | Lung Tissue Concentrations |
| A | p.o., 15 mg/kg, q.d. | 133 ng/mL | 172 ng/mL |
| B | i.h., 15 mg/mL for 3 min, q.d. | 80.9 ng/mL | 590 ng/mL |
| C | i.h., 50 mg/mL for 3 min, q.d. | 168 ng/mL | 1396 ng/mL |

After 5 days of oral dosing at 15 mg/kg, itraconazole levels in lung tissues were about 1.3× of that in plasma, showing a moderate accumulation in lung as compared to systemic circulation.

After 5 days of inhalation at 15 mg/mL for 3 min, itraconazole levels in lung tissues were about 7.3× of that in plasma, showing a significant increase in lung as result of the direct dosing route. Similarly, at the inhalation dose of 50 mg/mL for 3 min, the differences were 8.3× in favor of lung tissue.

This study was designed to demonstrate that by administering itraconazole directly to lung tissues via inhalation the safety window of anti-IPF treatment can be further widened.

The results from this study established that itraconazole administered via inhalation is efficacious against bleomycin induced IPF in mice in a dose-proportional fashion. All indicators, from collagen content in BALF to inflammatory cell counts, to histopathological images, showed significant improvement by the end of the study. Signs of further improvements compared to oral dosing of the same drug were observed. Analysis of lung tissues and plasma samples showed the observed efficacies are more likely driven by the exposures of the drug in lung tissues, but not the exposures of the drug in plasma. After oral dosing, itraconazole levels in lung tissues was slightly higher than those in plasma, making itraconazole the antifungal of choice for lung infections. However, inhalation greatly enhanced lung tissue exposure, and likely accounted for extra anti-IPF activities observed. The inhalation formulation and device have not been optimized, and further research and development is warranted.

Because of the greatly enhanced ratios of lung tissue concentration vs. plasma concentration after inhalation of itraconazole, and its anti-IPF activities is most likely driven by its exposure in lung tissue, the safety window of itraconazole through inhalation is likely to be expanded significantly as compared to oral dosing, and making inhalation a very attractive alternative, especially for chronic treatment, which is very likely required for most IPF patients.

I claim:

1. A method for reducing the severity of idiopathic pulmonary fibrosis (IPF) in a patient in need thereof, said method comprising:

administering by inhalation comprises administering an inhaled dose of an aqueous solution of itraconozole (ITA) having a concentration of ITA from 0.1 mg/mL to 60 mg/ml for 3 minutes, the method resulting in reduction in fibrotic activity in the patient, wherein the inhaled dose is administered with a liquid nebulizer, and the administering of the inhaled dose with the liquid nebulizer;

(i) achieves lung deposition of at least 7% of the ITA administered to the patient;

(ii) provides a Geometric Standard Deviation (GSD) of emitted droplet size distribution of the aqueous solution of 1.0 μm to 2.5 μm;

(iii) provides:

a) a mass median aerodynamic diameter (MMAD) of droplet size of the aqueous solution emitted with the liquid nebulizer of 1 μm to 5 μm;

b) a volumetric mean diameter (VMD) of 1 μm to 5 μm; and/or c) a mass median diameter (MMD) of 1 μm to 5 μm; or (iv) provides a fine particle fraction (FPF=% less than or equal to 55 μm) of droplets emitted from the liquid nebulizer of at least 30%, and wherein:

the lung tissue Cmax of ITA from the inhaled dose is at least equivalent to, or greater than, a lung tissue Cmax of up to 801 mg of an orally administered dosage of ITA; and/or the blood $AUC_{0-24}$ of ITA from the inhaled dose directly administered to the lungs of the mammal is less than or equivalent to the blood $AUC_{0-24}$ of up to 801 mg of an orally administered dosage of ITA.

2. The method of claim 1, wherein the administering by inhalation comprises administering by inhalation of particles or droplets comprising ITA and having a diameter of 1.0 to 2.5 microns.

3. The method of claim 1, wherein the administering by inhalation comprises administering by inhalation of aqueous droplets.

4. The method of claim 3, wherein the administering by inhalation comprises administering an inhaled dose comprising from 0.4 to 240 ml of the aqueous solution of ITA.

5. The method of claim 1, wherein the concentration of ITA in the aqueous solution is 5 mg/ml to 50 mg/mL.

6. The method of claim 1, wherein the administering by inhalation comprises administering by inhalation of nanoparticles comprising ITA and having an effective average particle size less than 1000 nm.

7. The method of claim 6, wherein the administering by inhalation comprises administering by inhalation of liposomes comprising ITA and having a diameter between 80 to 300 nm.

8. The method of claim 1, wherein the administering by inhalation comprising administering by inhalation of microparticles comprising ITA wherein the size distribution of microparticles is 90% are less than 5 microns and 95% are less than 10 microns.

9. The method of claim 1, further comprising administering an effective amount of an additional antifibrosis agent.

10. The method of claim 9, wherein the additional antifibrosis agent is pirfenidone or nintedanib.

* * * * *